(12) United States Patent
Wolkenberg et al.

(10) Patent No.: US 9,260,413 B2
(45) Date of Patent: *Feb. 16, 2016

(54) INHIBITORS OF CATECHOL O-METHYL TRANSFERASE AND THEIR USE IN THE TREATMENT OF PSYCHOTIC DISORDERS

(71) Applicant: Merck Sharp & Dohme Corp., Rahway, NJ (US)

(72) Inventors: Scott Wolkenberg, Jenkintown, PA (US); Scott T. Harrison, Glenside, PA (US); James C. Barrow, Arnold, MD (US); Zhijan Zhao, Hatfield, PA (US); Jeffrey Melamed, North Wales, PA (US); Nathan R. Kett, Franklin, TN (US); Amy Zartman, West Point, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/502,582

(22) Filed: Sep. 30, 2014

(65) Prior Publication Data

US 2015/0024071 A1   Jan. 22, 2015

Related U.S. Application Data

(63) Continuation of application No. 13/582,637, filed on Mar. 13, 2013, now Pat. No. 8,969,364.

(51) Int. Cl.
| | |
|---|---|
| *A61K 45/06* | (2006.01) |
| *C07D 401/14* | (2006.01) |
| *C07D 239/54* | (2006.01) |
| *C07D 239/553* | (2006.01) |
| *C07D 401/10* | (2006.01) |

(52) U.S. Cl.
CPC ............. *C07D 401/14* (2013.01); *A61K 45/06* (2013.01); *C07D 239/54* (2013.01); *C07D 239/553* (2013.01); *C07D 401/10* (2013.01)

(58) Field of Classification Search
CPC .. C07D 401/14; C07D 239/54; C07D 401/10; C07D 239/553; A61K 45/06
See application file for complete search history.

(56) References Cited

U.S. PATENT DOCUMENTS

| | | | |
|---|---|---|---|
| 4,536,518 A  * | 8/1985 | Welch et al. .................. | 514/647 |
| 2010/0204237 A1 | 8/2010 | Mikamiyama et al. | |
| 2011/0301109 A1* | 12/2011 | Liu et al. ........................ | 514/35 |

FOREIGN PATENT DOCUMENTS

| | | |
|---|---|---|
| EP | 0663396 A1 | 7/1995 |
| JP | 2005-511543 A | 4/2005 |
| WO | 03/035077 A1 | 1/2003 |
| WO | 2005061490 A1 | 7/2005 |

OTHER PUBLICATIONS

RN 1194473-20-5, Casreact 151:520198, Coordination Chemistry Based Approach to Lipophilic Inhibitors of 1-Deoxy-D-xylulose-5-phosphate Reductoisomerase. Deng et al., Journal of Medicinal Chemistry, 52(21), pp. 6539-6542, 2009.
RN 766557-47-5, Casreact 141:307054, Active Site Inhibitors of HCV NS5B Polymerase. The Development and Pharmacophore of 2-thienyl-5, 6-dihydroxypyrimidine-4-carboxylic acid, Stansfield, et al., Bioorganic & Medicinal Chemistry Letters, 14(20), pp. 5085-5088, (English) 2004.
RN 127116-90-9, Casreact 112:216531, Preparation of Pyrimidine Derivatives with Potential Cardiotonic Activity, Kosary, et al., Acta Pharmaceutica Hungarica, 59(6), pp. 241-247 (Hungarian) 1989.
RN 13922-47-9, Casreact 66:94985, Pyrimidol [4,5-e]dihydro-1,3-oxazines and Related Compounds, O'Brien et al., Journal of Heterocyclic Chemistry, 4(1), pp. 49-53 (English) 1967.
RN 100133-51-5, Casreact 51:9388, Synthesis of 5-hydroxypyrimidines, Hull et al., Journal of the Chemical Society 2033-5 1956.
RN 99361-49-6, Casreact 51:9383, Synthesis of Divicine (2, 4-diamino-5, 6-dihydroxypyrimidine) and Other Derivatives of 4, 5 (5, 6)-dihydroxypyrimidine, Davoll, et al., Journal of the Chemical Society pp. 2124-2131, 1956.
Summa, V., HCV NS5b RNA-Dependent RNA Polymerase Inhibitors: From a,y-Diketoacids to 4,5-Dihydroxypyrimidine- or 3-Methyl-5-hydroxypyrimidinonecarboxylic Acids, Design and Synthesis, Journal of Medicinal Chemistry, 2004, 47(22), pp. 5336-5339.
Kirschberg TA et al., RNase H Active Site Inhibitors of Human Immunodeficiency Virus Type 1 Reverse Transcriptase: Design, Biochemical Activity, and Structural Information, Journal of Medicinal Chemistry, 2009, vol. 52, No. 19, pp. 5781-5784.
Pacini B. et al., 2-(3-Thienyl)-5,6-dihydroxypyrimidine-4-carboxylic Acids As Inhibitors of HCV NS5B RdRp, Bioorganic & Medicinal Chemistry Letters, 2009, vol. 19, No. 21, pp. 6245-6249.
Pedersen AH et al., N-Quaternary Compounds, Part LV. Synthetic Studies of the 2,3-Dihydrothiazolo[3,2-c] pyrimidinium-8-olate System, Acta Chemica Scandinavica B, vol. 37, No. 19839, pp. 947-951, 1983.

* cited by examiner

*Primary Examiner* — Alexander R Pagano
(74) *Attorney, Agent, or Firm* — Fox Rothschild LLP; Gerard P. Norton; Jin Zhu

(57) ABSTRACT

The present invention relates to 4-pyridinone compounds which are inhibitors of catechol O-methyltransferase (COMT), and are useful in the treatment and prevention of neurological and psychiatric disorders and diseases in which COMT enzyme is involved. The present invention also relates to pharmaceutical compositions comprising these compounds and the use of these compounds and compositions in the prevention or treatment of such diseases in which COMT is involved.

18 Claims, No Drawings

INHIBITORS OF CATECHOL O-METHYL TRANSFERASE AND THEIR USE IN THE TREATMENT OF PSYCHOTIC DISORDERS

CROSS REFERENCE TO RELATED APPLICATIONS

This application is a Continuation of U.S. patent application Ser. No. 13/528,637, filed Mar. 13, 2013, which is the National Stage of International Application No. PCT/US2011/026424, filed on Feb. 28, 2011, which claims the benefit under 35 U.S.C. 119(e) of U.S. Provisional Application Ser. No. 61/310,386, filed Mar. 4, 2010. The contents of all are hereby incorporated by reference in their entirety.

BACKGROUND OF THE INVENTION

The symptoms of schizophrenia are generally divided into three categories; positive, negative and cognitive. Positive symptoms include hallucinations, delusions and disorganized behavior while negative symptoms are characterized by a lack of pleasure and/or interest in life. Cognitive deficit includes difficulties in the organization of thoughts and prioritization of tasks. Patients with bipolar disorder generally display circular mood changes ranging from severe depression to severe mania with or without psychotic features. Schizophrenia and bipolar disorder are among the most severe forms of psychiatric disorders that elicit overlapping cognitive deficits (Tasman et al., Psychiatry, West Sussex, John Wiley & Sons, Ltd., Second Edition, Volume 1, 2003, pp 254-272; and Sadock and Sadock, Kaplan and Sadock's Comprehensive Textbook of Psychiatry, 7 ed., Vol. 1, 2005, Philadelphia, Pa.; Lippincott Williams & Wilkins, pp 236-272 and 1330-1395) and they tend to be chronic/progressive. In contrast to positive symptoms, the negative and cognitive symptoms of schizophrenia are thought to have a greater impact on long-term disability, treatment outcome and functional recovery (Addington and Addington, 1993; Green, 1996). Dissatisfaction with therapy is attributed to lack of efficacy or intolerable and unacceptable side affects. The side effects have been associated with significant metabolic, extrapyramidal, prolactic and cardiac adverse events. See, Lieberman et al., N. Engl. J. Med. (2005) 353:1209-1223.

While multiple pathways are believed to be involved in the pathogenesis of schizophrenia leading to negative and cognitive symptoms, much attention has focused on reduced dopamine neurotransmission in the prefrontal cortex (Weinberger, 1987; Weinberger et al., 1988; Akil et al., 1999). Evidence for reduced dopamine neurotransmission in the prefrontal cortex is supported by reduced regional cerebral blood flow or hypoactivation of the dorsolateral prefrontal cortex in schizophrenia patients (Weinberger et al., 1988; Daniel et al., 1991; Okubo et al., 1997; Abi-Dargham et al., 2002). Schizophrenia related prefrontal deficits, independent from treatment or psychotic state, have been correlated with poor performance in tasks of executive function (e.g. n-back or Wisconsin Card Sorting Test) that evaluate prefrontal engagement (Weinberger et al., 1986, 1988; Carter et al., 1998; Callicott et al., 2000; Barch et al., 2001). In addition to deficits in executive function, reduced dopamine neurotransmission in the prefrontal cortex is involved in several brain activities including; attention, hedonic activities, natural rewards, and biologic activities such as cell signaling. Therefore, a compound which selectively enhances dopamine neurotransmission within the prefrontal cortex may have therapeutic potential for the treatment of cognitive and negative symptoms.

Dopamine levels in the brain are determined by biosynthesis and release, as well as its rate of diffusion, reuptake, and degradation. Catechol-O-methyltransferase (COMT), is an important enzyme involved in the breakdown of dopamine in the cortex. COMT converts dopamine to 3-methoxytyramine and the dopamine metabolite dihydroxyphenylacetic acid (DOPAC) to homovanillic acid (HVA) (Boulton and Eisenhofer, 1998). In fact, COMT acts on a variety of biogenic catecholamines as well as catecholestrogens, dietary phytochemicals and ascorbic acid. In subcortical structures (e.g. striatum), dopaminergic signalling is primarily regulated by removal of dopamine from the synaptic cleft via rapid uptake by the dopamine transporter (DAT) and/or norepinephrine transporter (NET). Regulation of dopamine transmission in the prefrontal cortex is markedly different. DAT is less densely expressed in synapses within the prefrontal cortex where dopamine is eliminated by uptake through the NET, diffusion, or metabolism by COMT and monoamine oxidase (Mazei et al., 2002; Moron et al., 2002; Lewis et al., 2001; Sesack et al., 1998; Smiley et al., 1994). COMT inhibitors would therefore be predicted to selectively increase cortical dopaminergic signaling and thereby improve cognitive function.

The COMT gene is located in the chromosome 22q11.21 region which has been linked to schizophrenia, bipolar disorder, ADHD and substance dependency (Williams, et al. 2003 and Takahashi et al., 2003). There are two major isoforms of COMT, membrane-bound COMT (MB-COMT) is the predominant form involved in the degradation of synaptic frontal lobe dopamine in human brain (Lachman et al., Pharmacogenetics (1996). 6(3):243-250). The other form is soluble COMT (S-COMT) which is transcribed from a different promoter than MB-COMT and is otherwise identical to human MB-COMT minus 50 amino acids at the N-terminus of the protein. In humans, COMT activity is modulated by a single nucleotide polymorphism at Val158Met (MB-COMT). Due to differences in enzyme thermostability, homozygous Met carriers have lower COMT activity, heterozygotes exhibit intermediate activity and homozygous Val carriers have greater enzyme activity (Chen et al., 2004). Despite the differences observed in activity based on genotype, only a modest relationship between Val158Met genotype and cognitive performance has been demonstrated by meta-analysis in normal individuals, while no effect was observed in schizophrenia. Based on an inverted-U relationship thought to exist between dopamine receptor activation and prefrontal cortical functioning, these findings might be reconciled with the fact that disease state, along with multiple environmental and genetic factors, contribute to prefrontal efficiency and dopamine levels (reviewed in Tunbridge et al., Biol Psych, 2006).

Although clozapine, Zyprexa, Risperdal and other antipsychotic drugs have been useful for the treatment of positive and arguably the negative symptoms of schizophrenia and bipolar disorder, they have not been free from side effects such as agranulocytosis, sedation, weight gain, hyper-lipidemia and hyperglycemia, all of which limit their applications (Tasman et al., 2003; Sadock and Sadock 2005). Thus, there remains a need for medications that effectively treat negative symptoms and cognitive deficit, have no major side effects, and are effective in the treatment of schizophrenia, bipolar disorder, depression, substance dependency, and ADD/ADHD, etc. Such medications might also be used to reduce such symptoms when they occur as part of another psychiatric syndrome or when they are incidental to a neurological disorder.

SUMMARY OF THE INVENTION

The present invention relates to pyrimidinone compounds which are inhibitors of catechol O-methyltransferase (COMT) enzyme, and are useful in the treatment and prevention of neurological and psychiatric disorders and diseases in which COMT is involved.

The present invention also relates to pharmaceutical compositions comprising these compounds and the use of these compounds and compositions in the prevention or treatment of such diseases in which COMT enzyme is involved.

The present invention further relates to a method of treating symptoms associated with a psychiatric disorder, comprising administration of a pharmacologically effective dose of a composition comprising a pyrimidinone COMT inhibitor or a pharmaceutically acceptable salt thereof to a patient.

Still, the present invention relates to improving negative symptoms and cognitive deficit associated with schizophrenia, augmentation of the effects of anti-psychotics in treatment of positive symptoms of schizophrenia, in treatment of major depression, the depressive phase of bipolar disorder, DA deficiency-related diseases such as ADD/ADHD, and substance dependency (combat cravings associated with and/or addictions to abuse of alcohol, opiates, cocaine, marijuana, amphetamines, tobacco), The present invention also relates to a method for the treatment of tobacco addiction and the weight gain/food cravings associated with quitting smoking or the use of antipsychotics.

The present invention also relates to a method of enhancing cognition in head injuries and dementias.

These and other aspects of the invention will be realized upon closer inspection of the specification as a whole.

DETAILED DESCRIPTION OF THE INVENTION

The present invention relates to novel COMT inhibitors of formula I

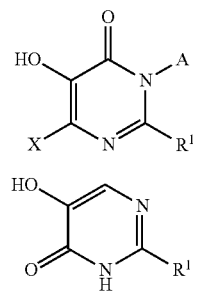

including tautomers or pharmaceutically acceptable salts and individual enantiomers and diastereomers thereof wherein:

A represents hydrogen, or $C_{1-6}$ alkyl, said alkyl optionally substituted with 1 to 3 groups of halo, OH, or Oalkyl;

X represents hydrogen, OH, halo, $C_{1-6}$ alkyl, $OC_{1-6}$ alkyl, $NR^2R^3$, $(CH_2)_nC_{6-10}$ aryl, $(CH_2)_nC_{5-10}$ heterocyclyl, said alkyl, aryl, and heterocyclyl optionally substituted with 1 to 3 groups of $R^a$;

$R^1$ represents $(CH_2)_nC_{6-10}$ aryl, or $(CH_2)_nC_{5-10}$ heterocyclyl, said aryl and heterocyclyl optionally substituted with 1 to 3 groups of $R^a$;

$R^2$ and $R^3$ independently represent H, OH, $C_{1-6}$ alkyl, $N(CH_3)_2$, $(CH_2)_nC_{5-10}$ heterocyclyl, $(CH_2)_nC_{6-10}$ aryl, said aryl and heterocyclyl optionally substituted with 1 to 3 groups of $R^a$;

$R^2$ and $R^3$ together with the nitrogen atom to which they are attached form a 5-10 membered ring that is optionally substituted with 1 to 3 groups of halo, OH, C2-6 alkenyl, $(CH_2)_nC_{5-10}$ heterocyclyl or $(CH_2)_nC_{6-10}$ aryl;

$R^a$ represents $C_{1-6}$ alkyl, halogen, hydroxyl, $C_{2-4}$alkynyl, $(CH_2)_nCF_3$, $OCHF_2$, $OCF_3$, $C_{3-6}$ cycloalkyl, $O(CH_2)_nC_{3-6}$ cycloalkyl, $NR^2C(O)R^2$, $C(O)N(R^2)_2$, $C(R^2)_2OR^2$, $C(O)R^2$, $NO_2$, CN, $N(R^2)_2$, $(CH_2)_nC(O)OR^2$, $SO_2R^2$, $NHSO_2R^2$, $OR^2$, $(CH_2)_nC_{5-10}$ heterocyclyl, $NH(CH_2)_nC_{5-10}$ heterocyclyl, $(CH_2)_nC_{6-10}$ aryl, $O(CH_2)_nC_{6-10}$ aryl, or $O(CH_2)_nC_{5-10}$ heterocyclyl, said alkyl, alkynyl, cycloalkyl, heterocyclyl and aryl optionally substituted with 1 to 3 groups of $R^b$:

$R^b$ represents $C_{1-6}$ alkyl, $OC_{1-6}$ alkyl, halogen, $CHF_2$, $OCHF_2$, —O—, $N(R^2)_2$, $C_2OH$, $S(O)_2NR^2R^3$, $(CH_2)_nC_{6-10}$ aryl, $(CH_2)_nC_{5-10}$ heterocyclyl, $C(O)(CH_2)_nC_{5-10}$ heterocyclyl, $NH(CH_2)_nC_{5-10}$ heterocyclyl, $C(O)NHC_{3-6}$ cycloalkyl, $OR^2$, $C_{3-6}$cycloalkyl, $(CH_2)_nCF_3$, or CN, said heterocyclyl optionally substituted with 1 or more of $C_{1-6}$ alkyl; and n represents 0 to 5.

An embodiment of the present invention is realized when A is hydrogen or methyl and all other variables are as originally described. A subembodiment of this invention is realized when A is hydrogen. Another subembodiment of this invention is realized when A is methyl.

Another embodiment of this invention is realized when X is hydrogen an all other variables are as originally described.

Still another embodiment of this invention is realized when $R^1$ is phenyl or pyridyl both optionally substituted with 1 to 3 groups of $R^a$ and all other variables are as originally described. A subembodiment of this invention is realized when $R^1$ is phenyl. Another subembodiment of this invention is realized when $R^1$ is pyridyl.

Yet another embodiment of this invention is realized when the $R^a$ substituent on $R^1$ is selected from the group consisting of H, $NHSO_2R^2$, halo, CN, $(CH_2)_nC_{6-10}$ aryl, $C_{5-10}$ heterocyclyl, $C_{2-4}$alkynyl, $OC_{1-6}$alkyl, and $OC_{6-10}$aryl, said alkyl, alkynyl, aryl and heterocyclyl optionally substituted with 1 to 3 groups of $R^b$.

Another embodiment of this invention is realized when the $R^b$ substituent on the $R^a$ of $R^1$ is selected from the group consisting of halo, $(CH_2)_nC_{6-10}$ aryl, $(CH_2)_nC_{5-10}$ heterocyclyl, $C_{1-6}$alkyl, $OC_{1-6}$alkyl, $OCHF_2$, and $CF_3$.

Another embodiment of this invention is realized wherein when the $R^a$ substituent on $R^1$ is a heterocyclyl it is selected from the group consisting of pyridyl, benzofuranyl, pyrazinyl, thiazolyl, pyridazinyl, pyrazolyl, pyrrolopyridyl, indolyl and benzimidazolyl, all of which are optionally substituted with 1 to 3 groups of $R^b$.

Another embodiment of this invention is realized by structural formula I:

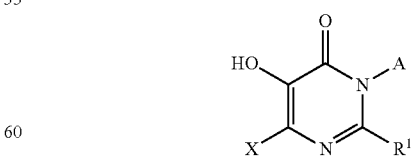

or pharmaceutically acceptable salts and individual enantiomers and diastereomers thereof wherein A, X and R1 are as previously described.

Still another embodiment of this invention is realized by structural formula Ia:

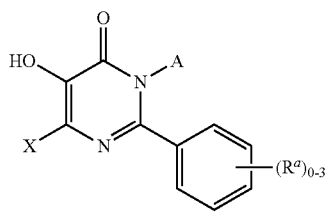

Ia or pharmaceutically acceptable salts and individual enantiomers and diastereomers thereof wherein A, X and $R^a$ are as previously described. A subembodiment of this invention is realized when A and X both are hydrogen, and $R^a$ is selected from the group consisting of $NHSO_2R^2$, halo, CN, $(CH_2)_n$ $C_{6-10}$ aryl, $C_{5-10}$ heterocyclyl, $C_{2-4}$ alkynyl, $OC_{1-6}$ alkyl, and $OC_{6-10}$ aryl, said alkyl, alkynyl, aryl and heterocyclyl optionally substituted with 1 to 3 groups of $R^b$, $R^2$ is as previously described and $R^b$ is selected from the group consisting of halo, $(CH_2)_nC_{6-10}$ aryl, $(CH_2)_nC_{5-10}$ heterocyclyl, $C_{1-6}$ alkyl, $OC_{1-6}$ alkyl, $OCHF_2$, and $CF_3$. Another subembodiment of the invention of structural formula Ia is realized wherein when the $R^a$ substituent on $R^1$ is a heterocyclyl it is selected from the group consisting of pyridyl, benzofuranyl, pyrazinyl, thiazolyl, pyridazinyl, pyrazolyl, pyrrolopyridyl, indolyl and benzimidazolyl, all of which are optionally substituted with 1 to 3 groups of $R^b$.

Still another embodiment of this invention is realized by structural formula Ib:

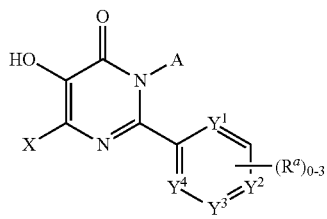

Ib or pharmaceutically acceptable salts and individual enantiomers and diastereomers thereof wherein A, X and $R^a$ are as previously described and one of $Y^1$, $Y^2$, $Y^3$ and $Y^4$ is N while the others are CH. A subembodiment of this invention is realized when $Y^2$ is N and $Y^1$, $Y^3$ and $Y^4$ are all CH. Another subembodiment of this invention is realized when A and X both are hydrogen, and $R^a$ is selected from the group consisting of $NHSO_2R^2$, halo, CN, $(CH_2)_nC_{6-10}$ aryl, $C_{5-10}$ heterocyclyl, $C_{2-4}$ alkynyl, $C_{1-6}$ alkyl, and $OC_{6-10}$ aryl, said alkyl, alkynyl, aryl and heterocyclyl optionally substituted with 1 to 3 groups of $R^b$, $R^2$ is as previously described and $R^b$ is selected from the group consisting of halo, $(CH_2)_nC_{6-10}$ aryl, $(CH_2)_nC_{5-10}$ heterocyclyl, $C_{1-6}$alkyl, $OC_{1-6}$alkyl, $OCHF_2$, and $CF_3$. Another subembodiment of the invention of structural formula Ib is realized wherein when the $R^a$ substituent on $R^1$ is a heterocyclyl it is selected from the group consisting of pyridyl, benzofuranyl, pyrazinyl, thiazolyl, pyridazinyl, pyrazolyl, pyrrolopyridyl, indolyl and benzimidazolyl, all of which are optionally substituted with 1 to 3 groups of $R^b$, Another embodiment of this invention is realized by structural formula II:

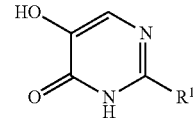

II or pharmaceutically acceptable salts and individual enantiomers and diastereomers thereof.

Still another embodiment of this invention is realized by structural formula IIa

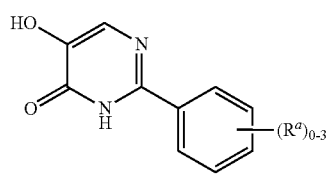

IIa or pharmaceutically acceptable salts and individual enantiomers and diastereomers thereof wherein $R^a$ is as previously described. A subembodiment of this invention is realized when $R^a$ is selected from the group consisting of $NHSO_2R^2$, halo, CN, $(CH_2)_nC_{6-10}$ aryl, $C_{5-10}$ heterocyclyl, $C_{2-4}$alkynyl, $OC_{1-6}$ alkyl, and $OC_{6-10}$aryl, said alkyl, alkynyl, aryl and heterocyclyl optionally substituted with 1 to 3 groups of $R^b$, $R^2$ is as previously described and $R^b$ is selected from the group consisting of halo, $(CH_2)_nC_{6-10}$ aryl, $(CH_2)_nC_{5-10}$ heterocyclyl, $C_{1-6}$ alkyl, $OC_{1-6}$alkyl, $OCHF_2$, and $CF_3$. Another subembodiment of the invention of structural formula IIa is realized wherein when the $R^a$ substituent on $R^1$ is a heterocyclyl it is selected from the group consisting of pyridyl, benzofuranyl, pyrazinyl, thiazolyl, pyridazinyl, pyrazolyl, pyrrolopyridyl, indolyl and benzimidazolyl, all of which are optionally substituted with 1 to 3 groups of $R^b$.

Still another embodiment of this invention is realized by structural formula IIb:

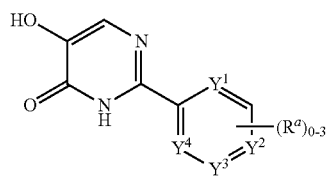

IIb or pharmaceutically acceptable salts and individual enantiomers and diastereomers thereof wherein $R^a$ is as previously described and one of $Y^1$, $Y^2$, $Y^3$ and $Y^4$ is N while the others are CH. A subembodiment of this invention is realized when $Y^2$ is N and $Y^1$, $Y^3$ and $Y^4$ are all CH. Another subembodiment of this invention is realized when $R^a$ is selected from the group consisting of $NHSO_2R^2$, halo, CN, $(CH_2)_nC_{6-10}$ aryl, $C_{5-10}$ heterocyclyl, $C_{2-4}$ alkynyl, $OC_{1-6}$alkyl, and $OC_{6-10}$aryl, said alkyl, alkynyl, aryl and heterocyclyl optionally substituted with 1 to 3 groups of $R^b$, $R^2$ is as previously described and $R^b$ is selected from the group consisting of halo, $(CH_2)_nC_{6-10}$ aryl, $(CH_2)_nC_{5-10}$ heterocyclyl, $C_{1-6}$ alkyl, $C_{1-6}$ alkyl, $OCHF_2$, and $CF_3$. Another subembodiment of the invention of structural formula IIb) is realized wherein when the $R^a$ substituent on $R^1$ is a heterocyclyl it is selected from the group consisting of pyridyl, benzofuranyl, pyrazinyl, thiazolyl, pyridazinyl, pyrazolyl, pyrrolopyridyl, indolyl and benzimidazolyl, all of which are optionally substituted with 1 to 3 groups of $R^b$.

Examples of compounds of this invention are found in Table 1:

| Compound #'s | Structure | IUPAC Name | Exact Mass $[M + H]^+$ |
|---|---|---|---|
| 1 | 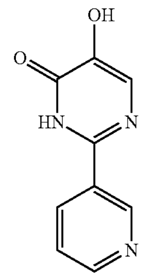 [SMILES: O=c1[nH]c(-c2cccnc2)ncc1O] | 5-hydroxy-2-pyridin-3-ylpyrimidin-4(3H)-one | Calc'd 190.1, found 190.1 |
| 2 | 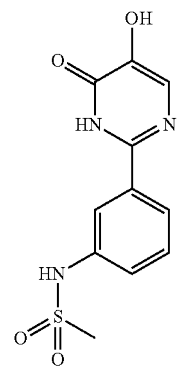 [SMILES: CS(=O)(=O)Nc1cccc(-c2ncc(O)c(=O)[nH]2)c1] | N-[3-(5-hydroxy-6-oxo-1,6-dihydropyrimidin-2-yl)phenyl]methanesulfonamide | Calc'd 282.1, found 282.1 |
| 3 | 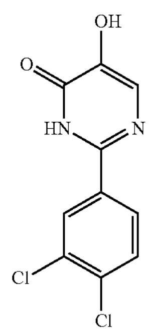 [SMILES: O=c1[nH]c(-c2ccc(Cl)c(Cl)c2)ncc1O] | 2-(3,4-dichlorophenyl)-5-hydroxypyrimidin-4(3H)-one | Calc'd 257.0, found 257.0 |
| 4 | 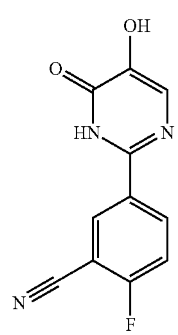 [SMILES: N#Cc1cc(-c2ncc(O)c(=O)[nH]2)ccc1F] | 2-fluoro-5-(5-hydroxy-6-oxo-1,6-dihydropyrimidin-2-yl)benzonitrile | Calc'd 232.1, found 232.1 |

-continued

| Compound #'s | Structure | IUPAC Name | Exact Mass [M + H]+ |
|---|---|---|---|
| 5 | 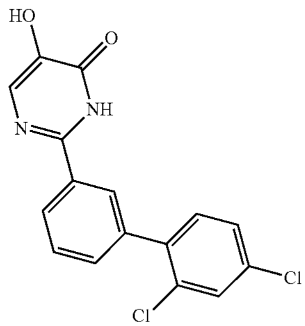 [SMILES: O=c1[nH]c(-c2cccc(-c3ccc(Cl)cc3Cl)c2)ncc1O] | 2-(2',4'-dichlorobiphenyl-3-yl)-5-hydroxypyrimidin-4(3H)-one | Calc'd 333.0, found 333.0 |
| 6 | 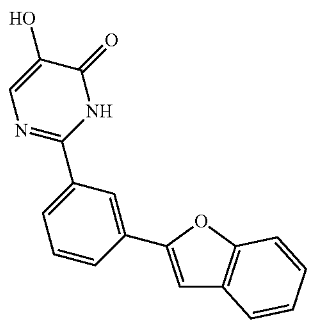 [SMILES: O=c1[nH]c(-c2cccc(-c3cc4ccccc4o3)c2)ncc1O] | 2[3-(1-benzofuran-2-yl)phenyl]-5-hydroxypyrimidiny-4(3H)-one | Calc'd 305.1, found 305.1 |
| 7 | 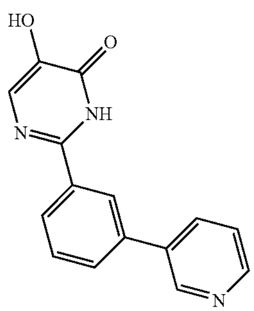 [SMILES: O=c1[nH]c(-c2cccc(-c3cccnc3)c2)ncc1O] | 5-hydroxy-2-[3-(pyridin-3-yl)phenyl]pyrimidin-4(3H)-one | Calc'd 266.1, found 266.1 |
| 8 | 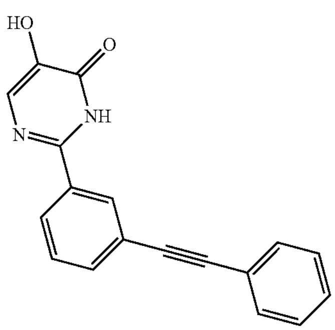 [SMILES: O=c1[nH]c(-c2cccc(C#Cc3ccccc3)c2)ncc1O] | 5-hydroxy-2-[3-(phenylethynyl)phenyl]pyrimidin-4(3H)-one | Calc'd 289.1, found 289.1 |
| 9 | 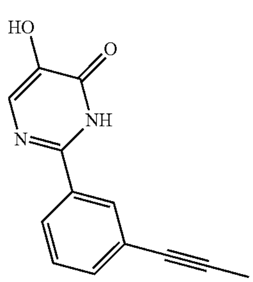 [SMILES: CC#Cc1cccc(-c2ncc(O)c(=O)[nH]2)c1] | 5-hydroxy-2-[3-(prop-1-yn-1-yl)phenyl]pyrimidin-4(3H)-one | Calc'd 277.1, found 277.1 |

-continued

| Compound #'s | Structure | IUPAC Name | Exact Mass [M + H]+ |
|---|---|---|---|
| 10 | 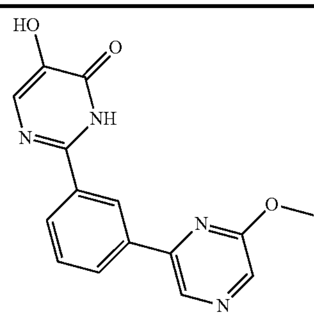 | 5-hydroxy-2-[3-(6-methoxypyrazin-2-yl)phenyl]pyrimidin-4(3H)-one | Calc'd 297.1, found 297.1 |
| 11 | 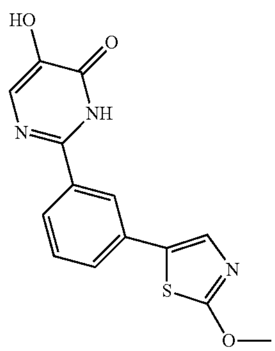 [SMILES: COc1ncc(-c2cccc(-c3ncc(O)c(=O)[nH]3)c2)s1] | 5-hydroxy-2-[3-(2-methoxy-1,3-thiazol-5-yl)phenyl]pyrimidin-4(3H)-one | Calc'd 302.1, found 302.1 |
| 12 | 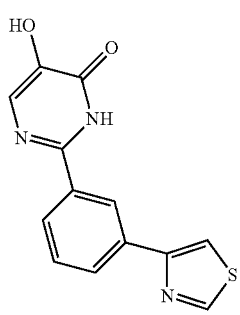 [SMILES: O=c1[nH]c(-c2cccc(-c3cscn3)c2)ncc1O] | 5-hydroxy-2-[3-(1,3-thiazol-4-yl)phenyl]pyrimidin-4(3H)-one | Calc'd 272.0, found 272.2 |
| 13 | 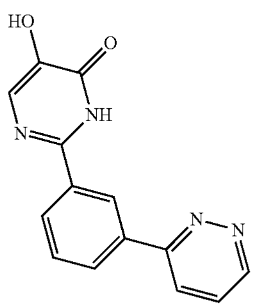 [SMILES: O=c1[nH]c(-c2cccc(-c3cccnn3)c2)ncc1O] | 5-hydroxy-2-[3-(pyridazin-3-yl)phenyl]pyrimidin-4(3H)-one | Calc'd 267.1, found 267.1 |

-continued

| Compound #'s | Structure | IUPAC Name | Exact Mass [M + H]+ |
|---|---|---|---|
| 14 | 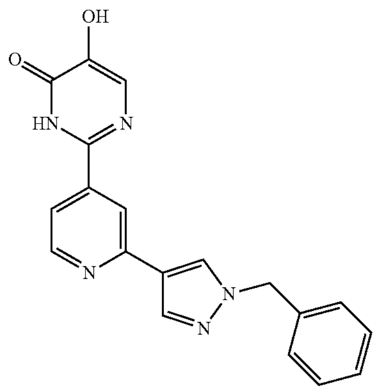 [SMILES: O=c1[nH]c(-c2ccnc(-c3cnn(Cc4ccccc4)c3)c2)ncc1O] | 2-[2-(3-benzyl-1H-pyrazol-4-yl)pyridin-4-yl]-5-hydroxypyrimidin-4(3H)-one | Calc'd 346.1, found 346.1 |
| 15 | 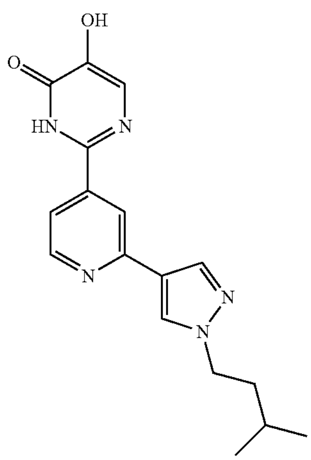 [SMILES: CC(C)CCn1cc(-c2cc(-c3ncc(O)c(=O)[nH]3)ccn2)cn1] | 5-hydroxy-2-{2-[1-(3-methylbutyl)-1H-pyrazol-4-yl]pyridin-4-yl}pyrimidin-4(3H)-one | Calc'd 326.2, found 326.1 |
| 16 | 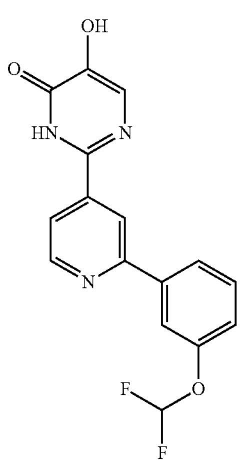 [SMILES: O=c1[nH]c(-c2ccnc(-c3cccc(OC(F)F)c3)c2)ncc1O] | 2-{2-[3-(difluoromethoxy)phenyl]pyridin-4-yl}-5-hydroxypyrimidin-4(3H)-one | Calc'd 332.1, found 332.1 |

-continued

| Compound #'s | Structure | IUPAC Name | Exact Mass [M + H]+ |
|---|---|---|---|
| 17 | 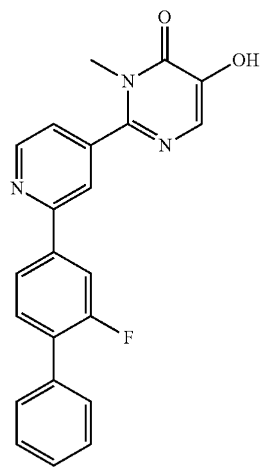 [SMILES: Cn1c(-c2ccnc(-c3ccc(-c4ccccc4)c(F)c3)c2)ncc(O)c1=O] | 2-[2-(2-fluorobiphenyl-4-yl)pyridin-4-yl]-5-hydroxy-3-methylpyrimidin-4(3H)-one | Calc'd 374.1, found 374.1 |
| 18 | 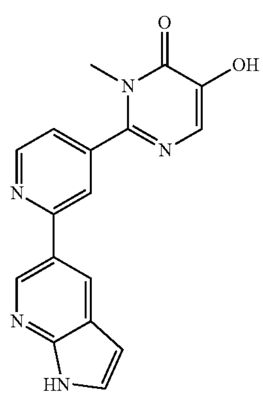 [SMILES: Cn1c(-c2ccnc(-c3cnc4[nH]ccc4c3)c2)ncc(O)c1=O] | 5-hydroxy-3-methyl-2-[2-(1H-pyrrolo[2,3-b]pyridin-5-yl)pyridin-4-yl]pyrimidin-4(3H)-one | Calc'd 320.1, found 320.1 |
| 19 | 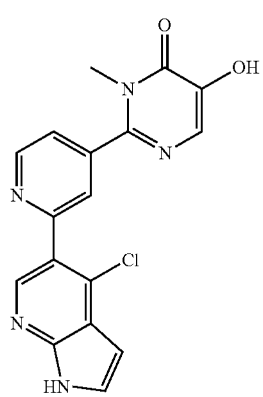 [SMILES: Cn1c(-c2ccnc(-c3cnc4[nH]ccc4c3Cl)c2)ncc(O)c1=O] | 2-[2-(4-chloro-1H-pyrrolo[2,3-b]pyridin-5-yl)pyridin-4-yl]-5-hydroxy-3-methylpyrimidin-4(3H)-one | Calc'd 354.1, found 354.1 |

-continued

| Compound #'s | Structure | IUPAC Name | Exact Mass [M + H]+ |
|---|---|---|---|
| 20 | 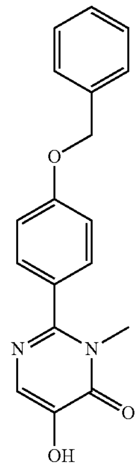 [SMILES: Cn1c(-c2ccc(OCc3ccccc3)cc2)ncc(O)c1=O] | 2-[4-(benzyloxy)phenyl]-5-hydroxy-3-methylpyrimidin-4(3H)-one | Calc'd 309.1, found 309.1 |
| 21 | 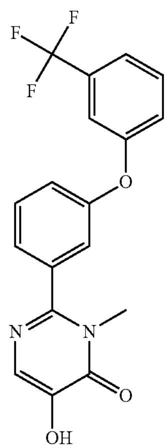 [SMILES: Cn1c(-c2cccc(Oc3cccc(C(F)(F)F)c3)c2)ncc(O)c1=O] | 5-hydroxy-3-methyl-2-{3-[3-(trifluoromethyl)phenoxy]phenyl}pyrimidin-4(3H)-one | Calc'd 363.1, found 363.2 |
| 22 | 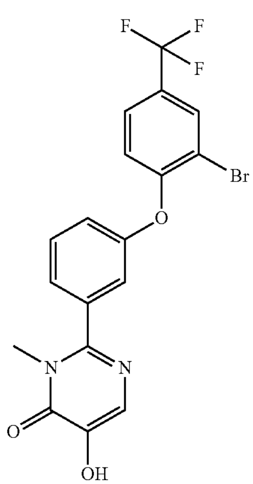 [SMILES: Cn1c(-c2cccc(Oc3ccc(C(F)(F)F)cc3Br)c2)ncc(O)c1=O] | 2-{3-[2-bromo-4-(trifluoromethyl)phenoxy]phenyl}-5-hydroxy-3-methylpyrimidin-4(3H)-one | Calc'd 441.0, found 441.0 |

-continued

| Compound #'s | Structure | IUPAC Name | Exact Mass [M + H]+ |
|---|---|---|---|
| 23 | 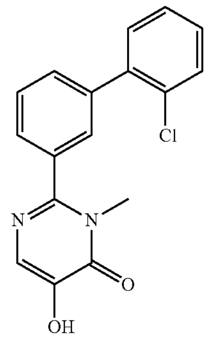 [SMILES: Cn1c(-c2cccc(-c3ccccc3Cl)c2)ncc(O)c1=O] | 2-(2'-chlorobiphenyl-3-yl)-5-hydroxy-3-methylpyrimidin-4(3H)-one | Calc'd 313.1, found 313.1 |
| 24 | 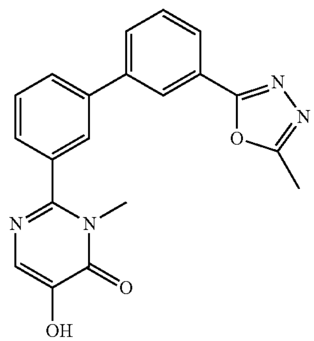 [SMILES: Cc1nnc(-c2cccc(-c3cccc(-c4ncc(O)c(=O)n4C)c3)c2)o1] | 5-hydroxy-3-methyl-2-[3'-(5-methyl-1,3,4-oxadiazol-2-yl)biphenyl-3-yl]pyrimidin-4(3H)-one | Calc'd 361.1, found 361.1 |
| 25 | 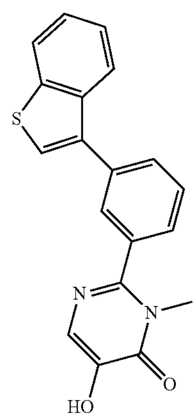 [SMILES: Cn1c(-c2cccc(-c3csc4ccccc34)c2)ncc(O)c1=O] | 2-[3-(1-benzothiophen-3-yl)phenyl]-5-hydroxy-3-methylpyrimidin-4(3H)-one | Calc'd 335.1, found 335.1 |
| 26 | 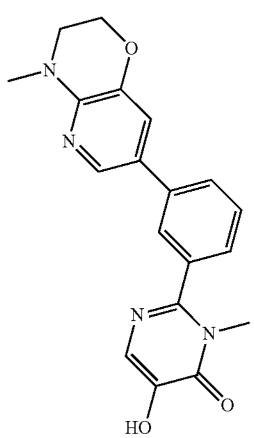 | 5-hydroxy-3-methyl-2-[3-(4-methyl-3,4-dihydro-2H-pyrido[3,2-b][1,4]oxazin-7-yl)phenyl]pyrimidin-4(3H)-one | Calc'd 351.1, found 351.1 |

-continued

| Compound #'s | Structure | IUPAC Name | Exact Mass [M + H]⁺ |
|---|---|---|---|
| 27 | 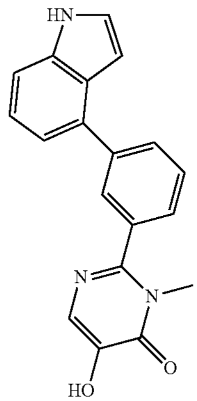 [SMILES: Cn1c(-c2cccc(-c3cccc4[nH]ccc34)c2)ncc(O)c1=O] | 5-hydroxy-2-[3-(1H-indol-4-yl)phenyl]-3-methylpyrimidin-4(3H)-one | Calc'd 318.1, found 318.1 |
| 28 | 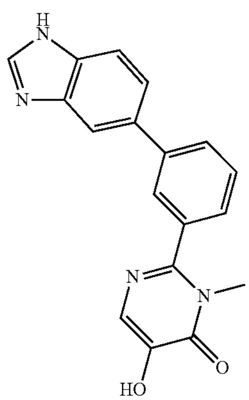 [SMILES: Cn1c(-c2cccc(-c3ccc4[nH]cnc4c3)c2)ncc(O)c1=O] | 2-[3-(1H-benzimidazol-5-yl)phenyl]-5-hydroxy-3-methylpyrimidin-4(3H)-one | Calc'd 319.1, found 319.1 |
| 29 | 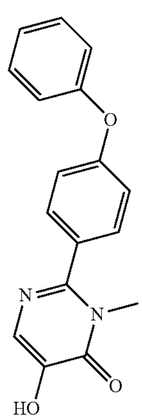 [SMILES: Cn1c(-c2ccc(Oc3ccccc3)cc2)ncc(O)c1=O] | 5-hydroxy-3-methyl-2-(4-phenoxyphenyl)pyrimidin-4(3H)-one | Calc'd 295.1, found 295.1 |
| 30 | | 5-hydroxy-3-methyl-2-(3-phenoxyphenyl)pyrimidin-4(3H)-one | Calc'd 295.1, found 295.1 | or pharmaceutically acceptable salts and individual enantiomers and diastereomers thereof.

When any variable (e.g. aryl, heterocycle, $R^1$, $R^3$ etc.) occurs more than one time in any constituent, its definition on each occurrence is independent at every other occurrence. Also, combinations of substituents/or variables are permissible only if such combinations result in stable compounds.

In addition, the compounds disclosed herein may exist as tautomers and both tautomeric forms are intended to be encompassed by the scope of the invention, even though only one tautomeric structure is depicted. For example, any claim to compound A or A' below is understood to include tautomeric structure B or B', and vice versa, as well as mixtures thereof.

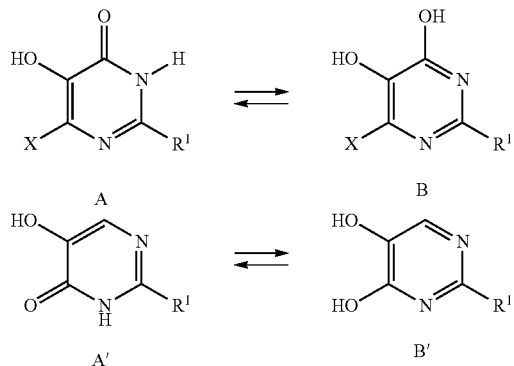

When $R^b$ is —O— and attached to a carbon it is referred to as a carbonyl group and when it is attached to a nitrogen (e.g., nitrogen atom on a pyridyl group) or sulfur atom it is referred to a N-oxide and sulfoxide group, respectively.

As used herein, "alkyl" encompasses groups having the prefix "alk" such as, for example, alkoxy, alkanoyl, alkenyl, and alkynyl and means carbon chains which may be linear or branched or combinations thereof. Examples of alkyl groups include methyl, ethyl, propyl, isopropyl, butyl, sec- and tert-butyl, pentyl, hexyl, and heptyl. "Alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl. Preferably, alkenyl is $C_2$-$C_6$ alkenyl. Preferred alkynyls are $C_2$-$C_6$ alkynyl.

"Alkenyl," "alkynyl" and other like terms include carbon chains containing at least one unsaturated C—C bond.

As used herein, "fluoroalkyl" refers to an alkyl group as described herein containing at least one fluorine substituent.

The term "cycloalkyl" refers to a saturated hydrocarbon containing one ring having a specified number of carbon atoms. Examples of cycloalkyl include cyclopropyl, cyclobutyl, cyclopentyl, and cyclohexyl.

The term "$C_{1-6}$" includes alkyls containing 6, 5, 4, 3, 2, or 1 carbon atoms The term "alkoxy" as used herein, alone or in combination, includes an alkyl group connected to the oxy connecting atom. The term "alkoxy" also includes alkyl ether groups, where the term 'alkyl' is defined above, and 'ether' means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as 'dimethyl ether'), and methoxyethane (also referred to as 'ethyl methyl ether').

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term heterocycle, heterocyclyl, or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

In certain other embodiments, the heterocyclic group is fused to an aryl or heteroaryl group. Examples of such fused heterocycles include, without limitation, tetrahydroquinolinyl and dihydrobenzofuranyl.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

Examples of heterocycloalkyls include azetidinyl, pyrrolidinyl, piperidinyl, piperazinyl, morpholinyl, tetrahydrofuranyl, imidazolinyl, pyrolidin-2-one, piperidin-2-one, and thiomorpholinyl.

The term "heteroatom" means O, S or N, selected on an independent basis.

A moiety that is substituted is one in which one or more hydrogens have been independently replaced with another chemical substituent. As a non-limiting example, substituted phenyls include 2-flurophenyl, 3,4-dichlorophenyl, 3-chloro-4-fluoro-phenyl, 2,4fluor-3-propylphenyl. As another non-limiting example, substituted n-octyls include 2,4 dimethyl-5-ethyl-octyl and 3-cyclopentyloctyl. Included within this definition are methylenes (—CH$_2$—) substituted with oxygen to form carbonyl (—CO—).

Unless otherwise stated, as employed herein, when a moiety (e.g., cycloalkyl, hydrocarbyl, aryl, alkyl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—), nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:
(a) halo, cyano, oxo, carboxy, formyl, nitro, amino, amidino, guanidino, and
(b) $C_1$-$C_6$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $SO_2CF_3$, $CF_3$, $SO_2Me$, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$alkylsulfinyl, arylalkylsulfnyl, arylsulfnyl, $C_1$-$C_8$ alkylsulfonyl, arylalkylsulfonyl, arylsulfonyl, $C_0$-$C_6$ N-alkylcarbamoyl, $C_2$-$C_{15}$ N,N dialkylcarbamoyl, $C_3$-$C_7$ cycloalkyl, aroyl, acyloxy, arylalkyl ether, aryl, aryl fused to a cycloalkyl or heterocycle or another aryl ring, $C_3$-$C_7$ heterocycle, or any of these rings fused or spiro-fused to a cycloalkyl, heterocyclyl, or aryl, wherein each of the foregoing is further optionally substituted with one more moieties listed in (a), above.

"Halogen" and "Halo" refers to fluorine, chlorine, bromine and iodine.

The term "mammal" "mammalian" or "mammals" includes humans, as well as animals, such as dogs, cats, horses, pigs and cattle.

All patents, patent applications and publications cited herein, whether supra or infra, are hereby incorporated by reference in their entirety and are deemed representative of the prevailing state of the art.

As used in this specification and the appended claims, the singular forms "a," "an" and "the" include plural references unless the content clearly dictates otherwise. Thus, for example, reference to "a primer" includes two or more such primers, reference to "an amino acid" includes more than one such amino acid, and the like.

The phrases "effective amount" or "therapeutically effective amount" mean a concentration of COMT enzyme complex modulator sufficient to inhibit or enhance the effect of the COMT enzyme complex.

"Treating" or "treatment of" a disease state includes: 1) preventing the disease state, i.e. causing the clinical symptoms of the disease state not to develop in a subject that may be exposed to or predisposed to the disease state, but does not yet experience or display symptoms of the disease state; 2) inhibiting the disease state, i.e., arresting the development of the disease state or its clinical symptoms; 3) or relieving the disease state, i.e., causing temporary or permanent regression of the disease state or its clinical symptoms.

Compounds described herein may contain one or more double bonds and may thus give rise to cis/trans isomers as well as other conformational isomers. The present invention includes all such possible isomers as well as mixtures of such isomers unless specifically stated otherwise.

The compounds of the present invention may contain one or more asymmetric centers and may thus occur as racemates, racemic mixtures, single enantiomers, diastereomeric mixtures, and individual diastereomers.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

It will be understood that, as used herein, references to the compounds of structural formula I are meant to also include the pharmaceutically acceptable salts, and also salts that are not pharmaceutically acceptable when they are used as precursors to the free compounds or in other synthetic manipulations.

The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N, N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and tromethamine.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like.

In a specific embodiment, compounds of the present invention provide a method for treating schizophrenia or psychosis comprising administering to a patient in need thereof an effective amount of a compound of the present invention. The Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, cannabis, cocaine, hallucinogens, inhalants, opioids, phencyclidine, ketamine and other dissociative anaesthetics, and other psychostimulants), psychosispsychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another specific embodiment, the compounds of the present invention provide a method for treating cognitive disorders comprising administering to a patient in need thereof an effective amount of a compound of the present invention. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemic, multi-infarct dementia, trauma, intracranial tumors, cerebral trauma, vascular problems or stroke, alcoholic dementia or other drug-related dementia, AIDS, HIV disease, Parkinson's disease, Huntington's disease, Pick's disease, Creutzfeldt Jacob disease, perinatal hypoxia, other general medical conditions or substance abuse), Alzheimer's disease, multi-infarct dementia, AIDS-related dementia, and Fronto temporal dementia, delirium, amnestic disorders or age related cognitive decline.

In another specific embodiment, compounds of the present invention provide a method for treating anxiety disorders comprising administering to a patient in need thereof an effective amount of a compound of the present invention. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced, anxiety disorder and anxiety due to a general medical condition.

In another specific embodiment, compounds of the present invention provide a method for treating substance-related disorders and addictive behaviors comprising administering to a patient in need thereof an effective amount of a compound of the present invention. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, cannabis, cocaine, hallucinogens, inhalants, nicotine, opioids, phencyclidine, sedatives, hypnotics or anxiolytics.

In another specific embodiment, compounds of the present invention provide a method for treating obesity or eating disorders associated with excessive food intake, and complications associated therewith, comprising administering to a patient in need thereof an effective amount of a compound of the present invention. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-10 and DSM-IV-TR and the term is intended to include similar disorders described in other sources. Disorders and conditions encompassed herein include, but are not limited to, obesity, bulimia nervosa and compulsive eating disorders.

In another specific embodiment, compounds of the present invention provide a method for treating mood and depressive disorders comprising administering to a patient in need thereof an effective amount of a compound of the present invention. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with postpartum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder (PDD), mood disorders due to a general medical condition, and substance-induced mood disorders. In another specific embodiment, compounds of the present invention provide a method for treating pain comprising administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain. In other specific embodiments, compounds of the invention provide methods for treating other types of cognitive, learning and mental related disorders including, but not limited to, learning disorders, such as a reading disorder, a mathematics disorder, or a disorder of written expression, attention-deficit/hyperactivity disorder, age-related cognitive decline, pervasive developmental disorder including autistic disorder, attention disorders such as attention-deficit hyperactivity disorder (ADHD) and conduct disorder; an NMDA receptor-related disorder, such as autism, depression, benign forgetfulness, childhood learning disorders and closed head injury; a neurodegenerative disorder or condition, such as neurodegeneration associated with cerebral trauma, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea (such as Sydenham's chorea, Huntington's disease, benign hereditary chorea, neuroacanthocytosis, symptomatic chorea, drug-induced chorea and hemiballism), myoclonus (including, generalised myoclonus and focal myoclonus), tics (including, simple tics, complex tics and symptomatic tics), dystonia (including, generalised, iodiopathic, drug-induced, symptomatic, paroxymal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy.

Of the disorders above, the treatment of schizophrenia, bipolar disorder, depression, including unipolar depression, seasonal depression and post-partum depression, premenstrual syndrome (PMS) and premenstrual dysphoric disorder (PDD), learning disorders, pervasive developmental disorders, including autistic disorder, attention disorders including Attention-Deficit/Hyperactivity Disorder, autism, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

The subject compounds are further useful in a method for the prevention, treatment, control, amelioration, or reduction of risk of the diseases, disorders and conditions noted herein.

In another specific embodiment, compounds of the present invention provide a method for treating Parkinson's disease when co-administered with L-DOPA, with or without a aromatic L-amino acid decarboxylase inhibitor (AADC) such as carbidopa, by preventing COMT-mediated metabolism of L-DOPA.

The subject compounds are further useful in a method for the prevention, treatment, control, amelioration, or reduction of risk of the aforementioned diseases, disorders and conditions in combination with other agents. The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention may be desirable. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. Accordingly, the pharmaceutical compositions of the present invention include those that also contain one or more other active ingredients, in addition to a compound of the present invention. The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrirnidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, atypical antipsychotics, bentazepam, benzoctamine, brotizolam, bupropion, busprione, butabarbital, butalbital, capuride, carbocloral, chloral betaine, chloral hydrate, clomipramine, clonazepam, eloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexol) hydrochloride, other COMT inhibitors such as entacapone, MOA-B inhibitors, antioxidants, Ata adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidasc (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-$HT_{1A}$ agonists or antagonists, especially 5-$HT_{1A}$ partial agonists, and corticotropin releasing factor (CRF) antagonists, Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

COMT inhibitor drugs have a beneficial effect in ill individuals if the principle or minor cause of illness is due to frontal lobe hypodopaminergia for multiple reasons, including, but not limited to, COMT over activity. COMT inhibitors are expected to be more useful in individuals with hypomethylated MB-COMT promoter and/or Val/Val and Val/Met genotype than those with Met/Met genotype.

The medicinal products which are useful in the treatment of these diseases consist of COMT inhibitor drugs or MB-COMT inhibitors or a pharmaceutical salt thereof either alone or in the form of a composition in which it is combined with any other pharmaceutically compatible product, which may be inert or physiologically active. These medicinal products may be used orally, topically, parenterally or rectally.

In addition to primates, such as humans, a variety of other mammals can be treated according to the method of the present invention. For instance, mammals including, but not limited to, cows, sheep, goats, horses, dogs, cats, guinea pigs, or other bovine, ovine, equine, canine, feline, or rodent, such as mouse, species can be treated. However, the method can also be practiced in other species, such as avian species (e.g., chickens).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The terms "administration of" and or "administering a" compound should be understood to mean providing a compound of the invention or a prodrug of a compound of the invention to the individual in need of treatment.

Further, it is understood that compounds of this invention can be administered at prophylactically effective dosage levels to prevent the above-recited conditions and disorders, as well as to prevent other conditions and disorders associated with calcium channel activity.

The term "composition" as used herein is intended to encompass a product comprising specified ingredients in predetermined amounts or proportions, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by mixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art. By "pharmaceutically acceptable" it is meant the carrier, diluent or excipient must be compatible with the other ingredients of the formulation and not deleterious to the recipient thereof.

The subject compounds are further useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.001 to 10 mg/kg. of body weight daily are administered to the patient, e.g., humans and elderly humans. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Pharmaceutical compositions of the present invention suitable for parenteral administration may be prepared as solutions or suspensions of the active compounds in water. A suitable surfactant can be included such as, for example, hydroxypropylcellulose, Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage, and thus should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, and dusting powder. Further, the compositions can be in a form suitable for use in transdermal devices. These formulations may be prepared, utilizing a compound represented of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid, such as, for example, where the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, and preservatives (including anti-oxidants). Furthermore, other adjuvants can be included to render the formulation isotonic with the blood of the intended recipient. Compositions containing a compound of the invention, or pharmaceutically acceptable salts thereof, can also be prepared in powder or liquid concentrate form.

The abbreviations used herein have the following meanings (abbreviations not shown here have their meanings as commonly used unless specifically stated otherwise): Ac (acetyl), Bn (benzyl), Boc (tertiary-butoxy carbonyl), Bop reagent (benzotriazol-1-yloxy)tris(dimethylamino)phosonium hexafluorophosphate, DBU (1,8-diazabicyclo[5.4.0] undec -7-ene), LHMDS (lithium hexamethyldisilyl amide), DMSO (methyl sulfoxide), PPTS (pridinium p-toluenesulfonate), PD/C (palladium on carbon), HRMS high resolution mass spectrometry, DCM (dichloromethane), LDA (lithium diisopropylamide), HPLC (high performance liquid chromatography) DIPEA (diisopropylethyl amine), DMAP (4-(dimethylamino)pyridine), NMR (nuclear magnetic resonance); DMF (N,N-dimethylformamide), EDC (1-(3-dimethylaminopropyl)-3-ethylcarbodiimide hydrochloride), $Et_3N$ (triethylamine), GST (glutathione transferase), HOBt (1-hydroxybenzotriazole), LAH (lithium aluminum hydride), Ms (methanesulfonyl; mesyl; or $SO_2Me$), $M_sO$ (methanesulfonate or mesylate), NaHMDS (sodium hexamethyldisilazane), NBS (N-bromosuccinimide), NCS (N-chlorosuceinimide), NSAID (non-steroidal anti-inflammatory drug), PDE (Phosphodiesterase), Ph (Phenyl), r.t. or RT (room temperature), Rac (Racemic), SAM (aminosulfonyl; sulfonamide or $SO_2NH_2$), SPA (scintillation proximity assay), Th (2- or 3-thienyl), TFA (trifluoroacetic acid), THF (Tetrahydrofuran), TLC (thin layer chromatography), Tr or trityl(N-triphenylmethyl), $C_3H_5$ (Allyl), Me (methyl), Et (ethyl), n-Pr (normal propyl), i-Pr (isopropyl), n-Bu (normal butyl), i-Butyl (isobutyl), s-Bu (secondary butyl), t-Bu (tertiary butyl), c-Pr (cyclopropyl), c-Bu (cyclobutyl), c-Pen (cyclopentyl), c-Hex (cyclohexyl).

The present compounds can be prepared according to the procedures provided in the Examples. The following Examples further describe, but do not limit, the scope of the invention.

Unless specifically stated otherwise, the experimental procedures were performed under the following conditions: All operations were carried out at room or ambient temperature; that is, at a temperature in the range of 18-25° C., Inert gas protection was used when reagents or intermediates were air and moisture sensitive. Evaporation of solvent was carried out using a rotary evaporator under reduced pressure (600-4000Pascals: 4.5-30 mm Hg) with a bath temperature of up to 60° C. The course of reactions was followed by thin layer chromatography (TLC) or by high-pressure liquid chromatography-mass spectrometry (HPLC-MS), and reaction times are given for illustration only. The structure and purity of all final products were assured by at least one of the following techniques: TLC, mass spectrometry, nuclear magnetic resonance (NMR) spectrometry or microanalytical data. When given, yields are for illustration only. When given, NMR data is in the form of delta (δ) values for major diagnostic protons, given in parts per million (ppm) relative to tetramethylsilane (TMS) as internal standard, determined at 300 MHz, 400 MHz or 500 MHz using the indicated solvent. Conventional abbreviations used for signal shape are: s. singlet; d. doublet; t. triplet; m. multiplet; br. Broad; etc. In addition, "Ar" signifies an aromatic signal. Chemical symbols have their usual meanings; the following abbreviations are used: v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

The procedures described herein for synthesizing the compounds may include one or more steps of protecting group manipulations and of purification, such as, re-crystallization, distillation, column chromatography, flash chromatography, thin-layer chromatography (TLC), radial chromatography and high-pressure chromatography (HPLC). The products can be characterized using various techniques well known in the chemical arts, including proton and carbon-13 nuclear magnetic resonance ($^1H$ and $^{13}C$ NMR), infrared and ultraviolet spectroscopy (IR and UV), X-ray crystallography, elemental analysis and HPLC and mass spectrometry (HPLC-MS). Methods of protecting group manipulation, purification, structure identification and quantification are well known to one skilled in the art of chemical synthesis.

Appropriate solvents are those which will at least partially dissolve one or all of the reactants and will not adversely interact with either the reactants or the product. Suitable solvents are aromatic hydrocarbons (e.g., toluene, xylenes), halogenated solvents (e.g., methylene chloride, chloroform, carbontetmchloride, chlorobenzenes), ethers (e.g., diethyl ether, diisopropylether, tert-butyl methyl ether, diglyme, tetrahydrofuran, dioxane, anisole), nitriles (e.g., acetonitrile, propionitrile), ketones (e.g., 2-butanone, dithyl ketone, tert-butyl methyl ketone), alcohols (e.g., methanol, ethanol, n-propanol, iso-propanol, n-butanol, t-butanol), N,N-dimethyl formamide (DMF), dimethylsulfoxide (DMSO) and water. Mixtures of two or more solvents can also be used. Suitable bases are, generally, alkali metal hydroxides, alkaline earth metal hydroxides such as lithium hydroxide, sodium hydroxide, potassium hydroxide, barium hydroxide, and calcium hydroxide; alkali metal hydrides and alkaline earth metal hydrides such as lithium hydride, sodium hydride, potassium hydride and calcium hydride; alkali metal amides such as lithium amide, sodium amide and potassium amide; alkali metal carbonates and alkaline earth metal carbonates such as lithium carbonate, sodium carbonate, cesium carbonate, sodium hydrogen carbonate, and cesium hydrogen carbonate; alkali metal alkoxides and alkaline earth metal alkoxides such as sodium methoxide, sodium ethoxide, potassium tert-butoxide and magnesium ethoxide; alkali metal alkyls such as methyllithium, n-butyllithium, sec-butyllithium, t-bultyllithium, phenyllithium, alkyl magnesium halides, organic bases such as trimethylamine, triethylamine, triisopropylamine, N,N-diisopropylethyl amine, piperidine, N-methyl piperidine, morpholine, N-methyl morpholine, pyridine, collidines, lutidines, and 4-dimethylaminopyridine; and bicyclic amines such as DBU and DABCO.

It is understood that the functional groups present in compounds described in the examples below can be further manipulated, when appropriate, using the standard functional group transformation techniques available to those skilled in the art, to provide desired compounds described in this invention.

It is also understood that compounds of this invention contain one or more stereocenters that may be prepared as single enantiomers or diastereomers, or as mixtures containing two or more enantiomers or diastereomers in any proportion.

Other variations or modifications, which will be obvious to those skilled in the art, are within the scope and teachings of this invention. This invention is not to be limited except as set forth in the following claims.

Several methods for preparing the compounds of this invention are illustrated in the following Schemes and Examples. Starting materials are made according to procedures known in the art or as illustrated herein.

Reaction Schemes

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

GENERAL REACTION SCHEMES
Scheme 1

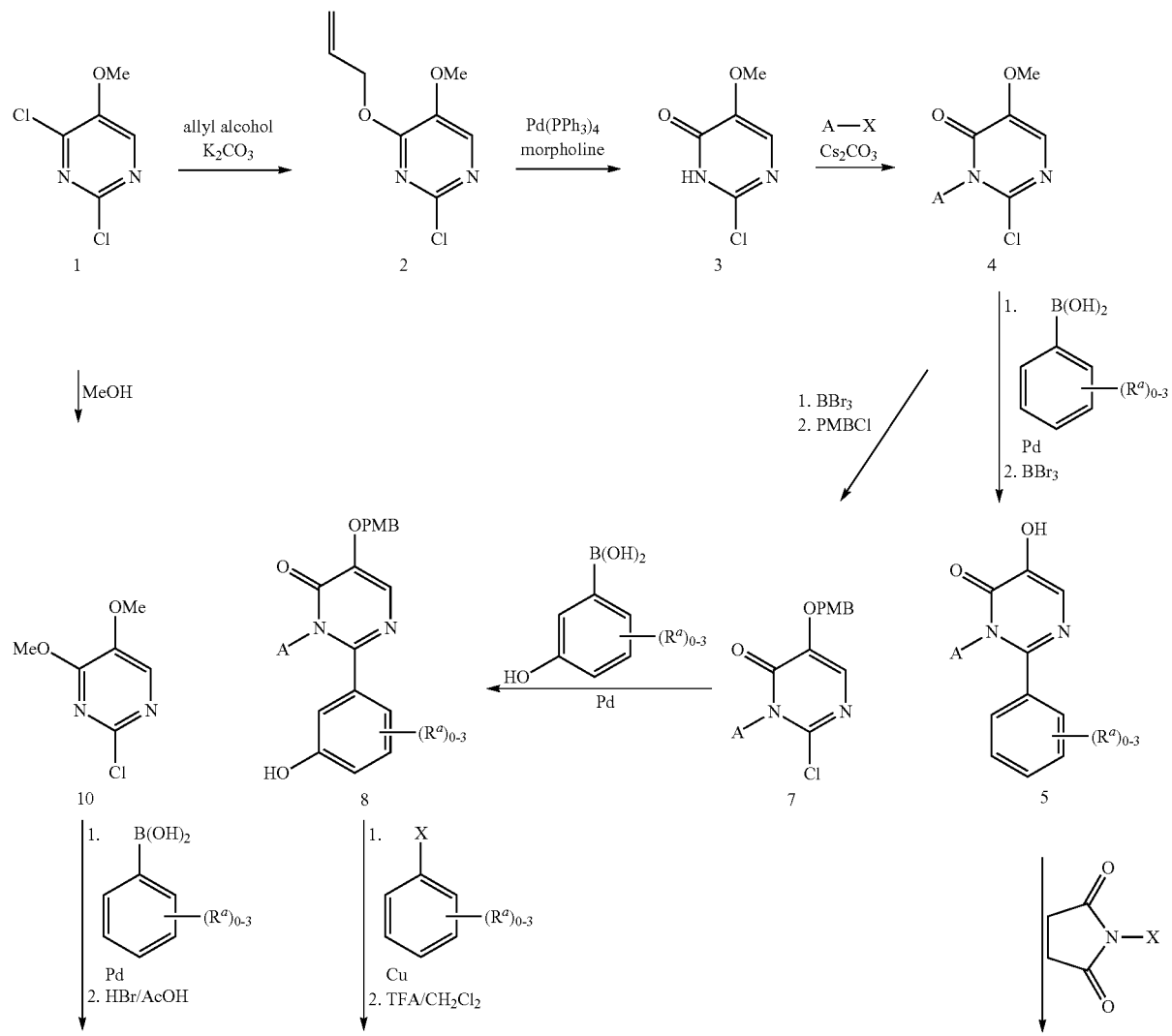

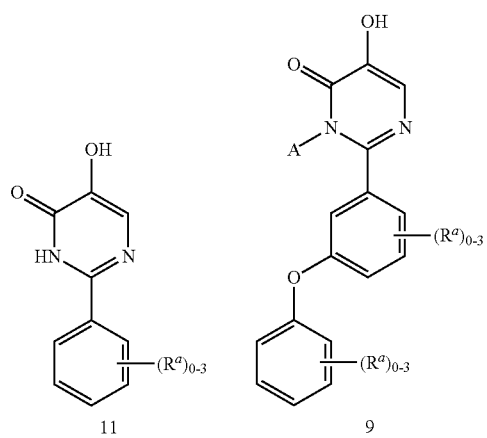

Compounds of the invention may be prepared as outlined in Scheme 1. Dichloropyrimidine 1 is converted to allyl ether 2 prior to Pd-mediated allyl deprotection and N-alkylation with introduction of substituent A to provide pyrimidinones 4. Compounds 4 are cross coupled to incorporate aryl and heteroaryl substituents and the resulting biaryls are treated with BBr$_3$ to effect methyl ether deprotection and afford target compounds 5. Compounds 5 can be further derivitized with incorporation of R$^1$ (when R$^1$=halogen) via treatment with N-halosuccinamides to furnish target compounds 6. Alternatively, compounds 4, after a protecting group switch, are cross coupled to incorporate substituted aromatics groups bearing a hydroxyl substituent as in compounds 8. These phenols are elaborated to biaryl ethers upon treatment with halogenated aromatics and Cu catalysts. Acidic cleavage of the PMB protecting group generates target compounds 9. Alternatively, compound 1 is converted to methyl ether 10 prior to cross coupling with incorporation of aryl and heteroaryl groups and methyl ether cleavage to furnish target compounds 11. Compounds of Scheme 1 can be further modified by manipulation of the substituent groups by general methods known in the art, including (but not limited to) cross coupling, oxidation, reduction, dealkylation, alkylation, acylation, and the like, and this modification may occur prior to or after deprotection.

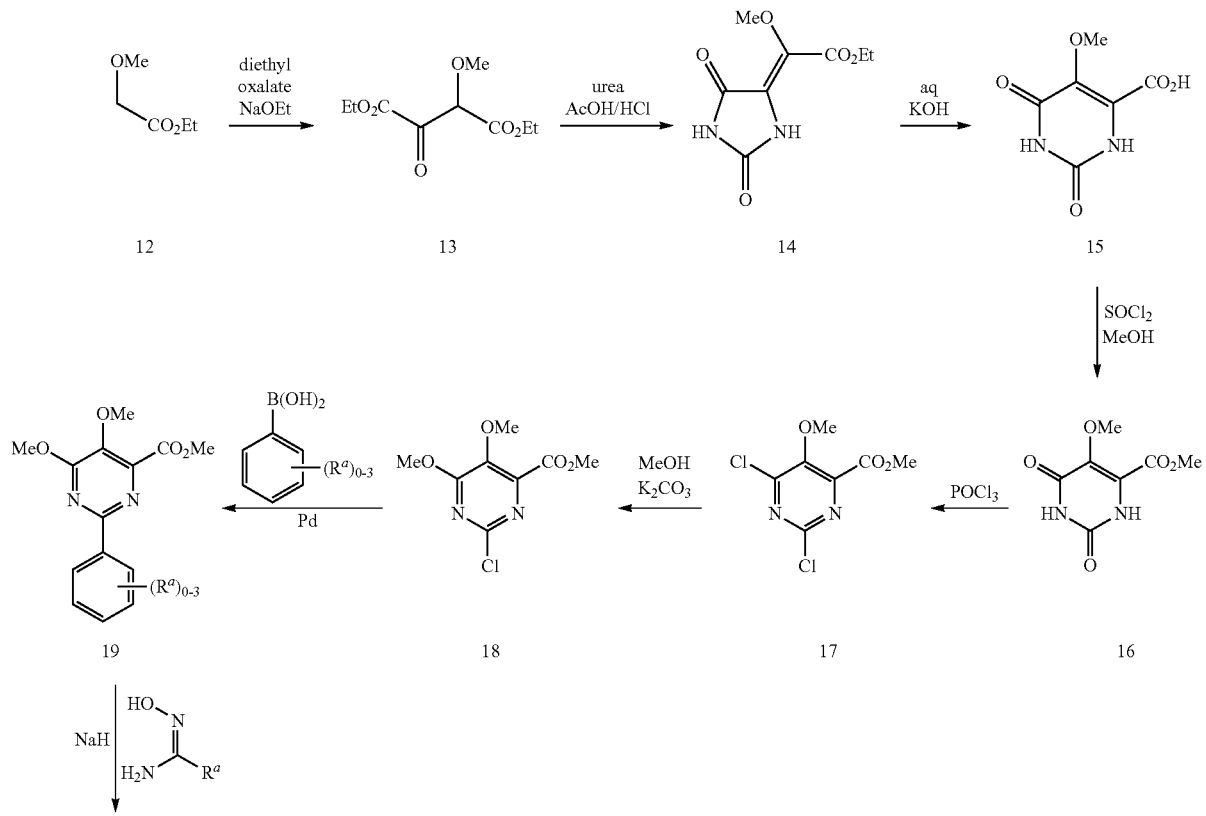

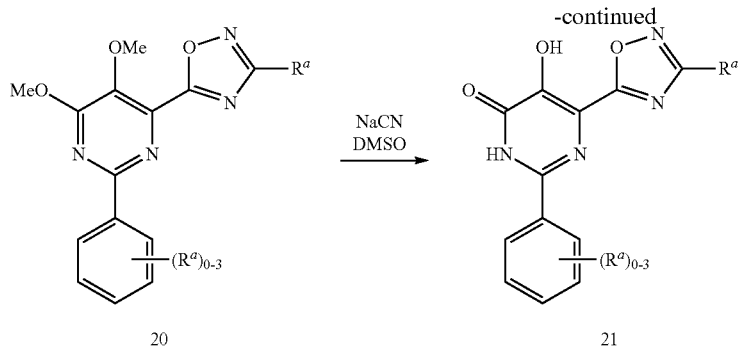

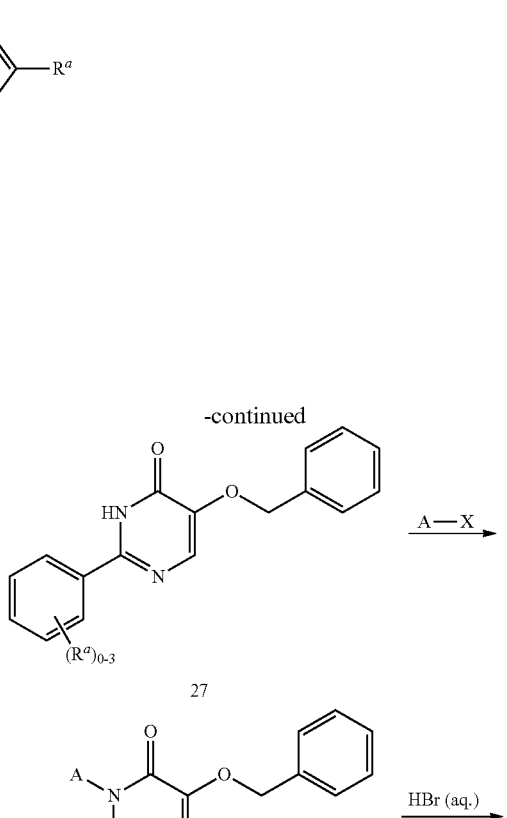

Compounds of the invention may be prepared as outlined in Scheme 2. Condensation of ethyl methoxyacetate 12 with diethyl oxalate is followed by cyclization with urea and ring expansion under basic conditions to provide dioxotetrahydropyrimidine 15. Conversion to the methyl ester, chlorination, and treatment with methanol provides dimethoxypyrimidine 18, which is cross coupled with substituted aromatics under Pd catalysis to afford compounds 19. Treatment with the anion of substituted amide oxime reagents generates 1,2,4-oxadiazoles 20 which after methyl ether deprotection provide target compounds 21. Compounds of Scheme 2 can be further modified by manipulation of the substitutent groups by general methods known in the art, including (but not limited to) cross coupling, oxidation, reduction, dealkylation, alkylation, acylation, and the like, and this modification may occur prior to or after deprotection.

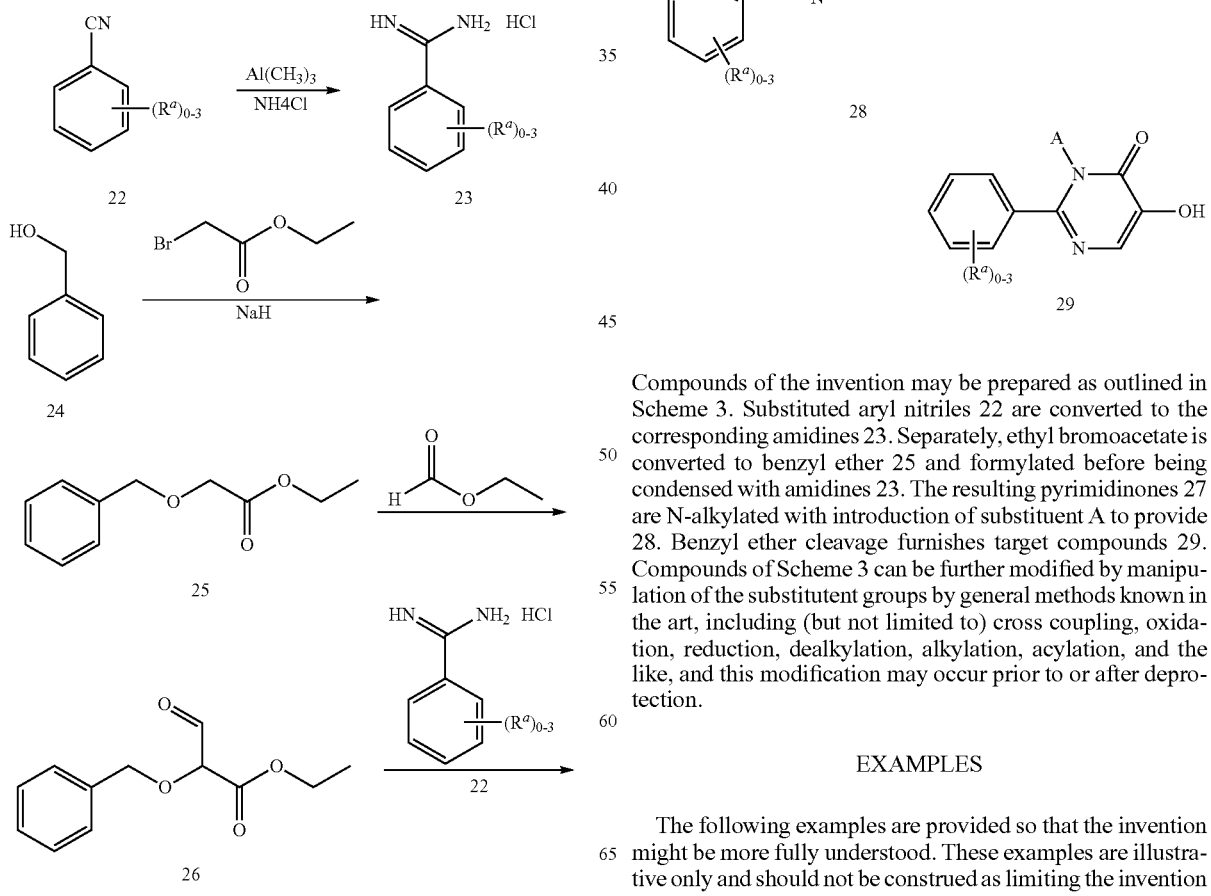

Compounds of the invention may be prepared as outlined in Scheme 3. Substituted aryl nitriles 22 are converted to the corresponding amidines 23. Separately, ethyl bromoacetate is converted to benzyl ether 25 and formylated before being condensed with amidines 23. The resulting pyrimidinones 27 are N-alkylated with introduction of substituent A to provide 28. Benzyl ether cleavage furnishes target compounds 29. Compounds of Scheme 3 can be further modified by manipulation of the substituent groups by general methods known in the art, including (but not limited to) cross coupling, oxidation, reduction, dealkylation, alkylation, acylation, and the like, and this modification may occur prior to or after deprotection.

EXAMPLES

The following examples are provided so that the invention might be more fully understood. These examples are illustrative only and should not be construed as limiting the invention in any way.

Example 1

2-[4-chloro-3-(trifluoromethyl)phenyl]-5-hydroxy-3-methylpyrimidin-4(3H)-one (1)

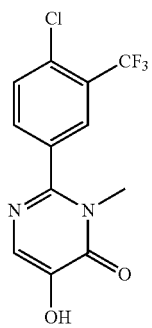

2-chloro-5-methoxy-4-(prop-2-en-1-yloxy)pyrimidine

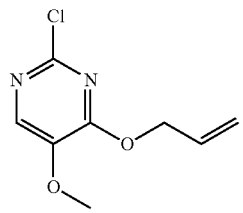

A mixture of 2,4-dichloro-5-methoxypyrimidine (85 g, 475 mmol), and K$_2$CO$_3$ (78.8 g, 570 mmol) in allyl alcohol (320 mL, 4.75 mol) was heated to 70° C. for 5 h before being cooled to r.t. and diluted with DCM, filtered through Celtic (DCM wash) and concentrated to give 95.0 g (99.7%) of 2-chloro-5-methoxy-4-(prop-2-en-1-yloxy)pyrimidine. $^1$H-NMR (CDC$_3$, 300 MHz) δ 7.85 (s, 1H), 6.09-5.99 (m, 1H), 5.43-5.38 (in, 1H), 5.31-5.27 (m, 1H), 4.91 (m, 2H), 3.87 (s, 3H). MS (ESI) m/z (M+H)$^+$ 201.0.

2-chloro-5-methoxypyrimidin-4(3H)-one

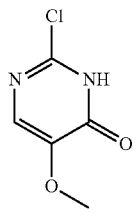

To a solution of 2-chloro-5-methoxy-4-(prop-2-en-1-yloxy)pyrimidine (95.0 g, 475 mmol) in anhydrous DCM (2 L) under nitrogen atmosphere was added morpholine (124 mL, 1.425 moL) and then Pd(Ph$_3$P)$_4$ (13.7 g, 11.9 mmol) and the reaction mixture was stirred at room temperature for 15 min. The reaction mixture was concentrated until thick, then poured into EtOAc. The precipitate was collected and dried to give 52 g of a mixture of 2-chloro-5-methoxypyrimidin-4(3H)-one and morpholine (1:1). $^1$H-NMR (CDC$_3$, 400 MHz) δ 7.45 (s, 1H), 3.67 (s, 3H). MS (ESI) m/z (M+H)$^+$ 161.0.

2-chloro-5-methoxy-3-methylpyrimidin-4(3H)-one

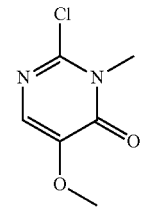

128 g (0.9 mol) of MeI was added dropwise to the suspension of 2-chloro-5-methoxypyrimidin-4(3H)-one (74 g, crude, about 0.3 mol) and Cs$_2$CO$_3$ (195 g, 0.6 mol) in 600 mL of DMF at 0° C. and the reaction mixture was stirred at this temperature for 1 h, then warmed to r.t., and stirred another 1 h. The mixture was poured into water and extracted with EtOAc several times. The extract was washed with water, brine and dried over Na$_2$SO$_4$ before being filtered and concentrated to give a crude product, which was purified by silica gel chromatography to give 31.2 g (71.2%) of 2-chloro-5-methoxy-3-methylpyrimidin -4(3H)-one. $^1$H-NMR (CDC$_3$, 400 MHz) δ 7.37 (s, 1H), 3.80 (s, 3H), 3.61 (s, 3H). MS (ESI) m/z (M+H)$^+$ 175.0/176.0.

2-[4-chloro-3-(trifluoromethyl)phenyl]-5-methoxy-3-methylpyrimidin-4(3H)-one

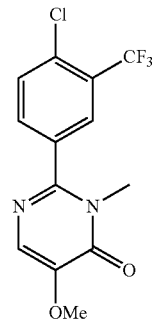 [SMILES: COc1cnc(-c2ccc(Cl)c(C(F)(F)F)c2)n(C)c1=O]

To a solution of 500 mg (2.86 mmol) 2-chloro-5-methoxy-3-methylpyrimidin-4(3H)-one in 10 ml THF was added 233 mg (0.286 mmol) 1,1'-bis(diphenylphosphino)ferrocene-palladium(II)dichloride dichloromethane adduct, 0.965 g (4.29 mmol) 4-chloro-3-(trifluoromethyl)benzeneboronic acid, and 1.87 g (5.73 mmol) Cs$_2$CO$_3$. The reaction mixture was heated to 130° C. for 15 min in the microwave, then diluted with 10 ml water, extracted with 30 ml EtOAc, dried over Na$_2$SO$_4$, filtered, and concentrated in vacuo. Purification by flash chromatography (25 g silica gel, 40-100% hexane/EtOAc) gave 625 mg (68% yield) of 2-[4-chloro-3-(trifluoromethyl)phenyl]-5-methoxy-3-methylpyrimidin-4(3H)-one. LCMS [M+H]$^+$=319.1.

2-[4-chloro-3-(trifluoromethyl)phenyl]-5-hydroxy-3-methylpyrimidin-4(3H)-one (1)

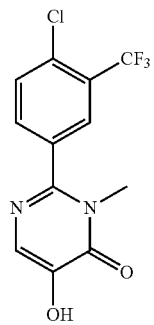

To a solution of 625 mg (1.96 mmol) 2-[4-chloro-3-(trifluoromethyl)phenyl]-5-methoxy-3-methylpyrimidin-4(3H)-one in 25 ml CH$_2$Cl$_2$ was added 5.88 ml (5.88 mmol) of a 1 M solution of BBr$_3$ in CH$_2$Cl$_2$. The reaction mixture was stirred for 1 h, then quenched with 25 ml MeOH, and concentrated in vacuo. Purification by HPLC gave 418 mg (70% yield) of 2-[4-chloro-3-(trifluoromethyl)phenyl]-5-hydroxy-3-methylpyrimidin-4(3H)-one. $^1$H NMR δ (ppm)(CDC$_3$): 7.86 (1 H, d, J=1.95 Hz), 7.73 (1 H, s), 7.67-7.61 (2 H, m), 3.54 (3 H, s). HRMS (ESI positive) calc (M+H)$^+$=305.0299. Found 305.0300.

Example 2

6-chloro-5-hydroxy-3-methyl-2-(4-phenoxyphenyl)pyrimidin-4(3H)-one (2)

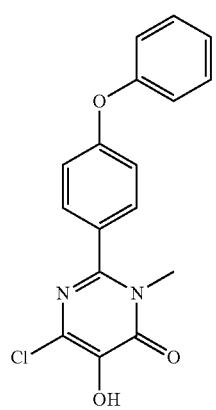

5-methoxy-3-methyl-2-(4-phenoxyphenyl)pyrimidin-4(3H)-one

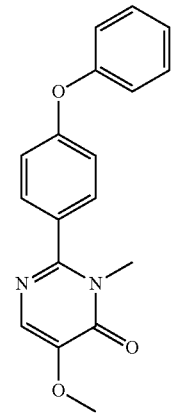 [SMILES: COc1cnc(-c2ccc(Oc3ccccc3)cc2)n(C)c1=O]

To a solution of 750 mg (4.30 mmol) 2-chloro-5-methoxy-3-methylpyrimidin-4(3H)-one in 20 ml THF was added 314 mg (0.430 mmol) 1,1'-bis(diphenylphosphino)ferrocene-palladium(H)dichloride dichloromethane adduct, 1.83 g (8.59 mmol) 4-phenoxyphenylboronic acid, and 4.30 ml (4.30 mmol) 1 M aq Cs$_2$CO$_3$. The reaction mixture was heated to 120° C. for 15 min in the microwave, then diluted with 10 ml water, extracted with 50 ml EtOAc, dried over Na$_2$SO$_4$, filtered, and concentrated in vacuo to give 1.33 g (100% yield) of crude 5-methoxy-3-methyl-2-(4-phenoxyphenyl)pyrimidin-4(3H)-one.

5-hydroxy-3-methyl-2-(4-phenoxyphenyl)pyrimidin-4(3H)-one

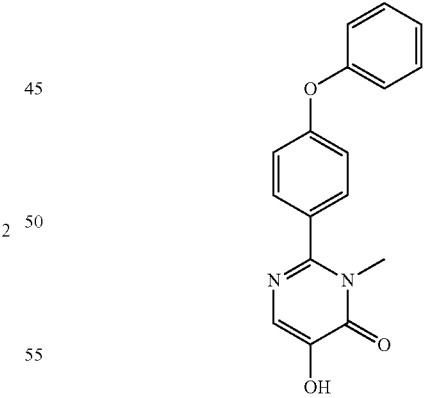

To a solution of 133 g (4.30 mmol) 5-methoxy-3-methyl-2-(4-phenoxyphenyl)pyrimidin-4(3H)-one in 25 ml CH$_2$Cl$_2$ was added 34.4 ml (34.4 mmol) of a 1 M solution of BBr$_3$ in CH$_2$Cl$_2$. The reaction mixture was stirred for 1 h, cooled to 0° C., quenched with 100 ml MeOH, and concentrated in vacuo. Purification by HPLC gave 945 mg (70% yield) of 5-hydroxy-3-methyl-2-(4-phenoxyphenyl)pyrimidin-4(3H)-one. LCMS [M+H]$^+$=295.1.

6-chloro-5-hydroxy-3-methyl-2-(4-phenoxyphenyl)pyrimidin-4(3H)-one (2)

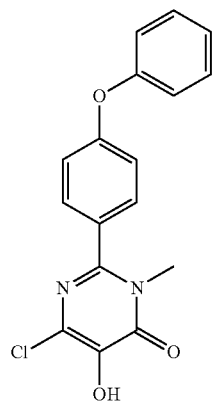

2

To a solution of 50 mg (0.170 mmol) 5-hydroxy-3-methyl-2-(4-phenoxyphenyl)pyrimidin-4(3H)-one in 850 µl CH₂Cl₂ was added 23.8 mg (0.178 mmol)N-chlorosuccinimide. The reaction mixture was heated to 50° C. for 12 h, then cooled to rt, and concentrated in vacuo. Purification by HPLC gave 10.0 mg (18% yield) of 6-chloro-5-hydroxy-3-methyl-2-(4-phenoxyphenyl)pyrimidin-4(3H)-one. ¹H NMR δ (ppm) (CDC₃): 7.48-7.46 (2 H, m), 7.41-7.38 (2 H, m), 7.19 (1 H, d, J=7.56 Hz), 7.09-7.05 (4 H, m), 6.43 (1 H, bs), 3.56 (3 H, s). FIRMS (ESI positive) calc (M+H)⁺=329.0687. Found 329.0693.

Example 3

2-biphenyl-3-yl-5-hydroxy-3-methylpyrimidin-4(3H)-one (3)

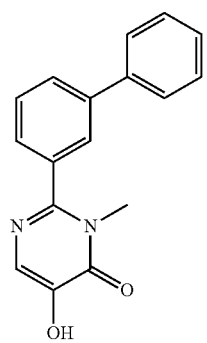

3

2-chloro-5-hydroxy-3-methylpyrimidin-4(3H)-one

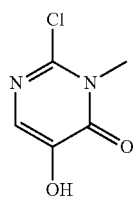

To a solution of 1.18 g (6.76 mmol) 2-chloro-5-methoxy-3-methylpyrimidin-4(3H)-one in 35 ml CH₂Cl₂ was added 47.3 ml (47.3 mmol) of a 1 M solution of BBr₃ in CH₂Cl₂. The reaction mixture was stirred for 1 h, cooled to 0° C., quenched with 100 ml MeOH, and concentrated in vacuo. The solid was suspended in ether, and collected by filtration to give 1.09 g (100% yield) of 2-chloro-5-hydroxy-3-methylpyrimidin-4(3H)-one. LCMS [M+H]⁺=161.0.

2-biphenyl-3-yl-5-hydroxy-3-methylpyrimidin-4(3H)-one (3)

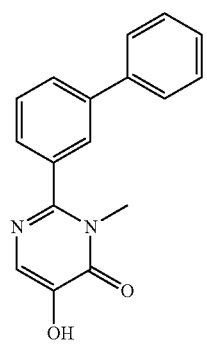

3

To a solution of 40 mg (0.249 mmol) 2-chloro-5-hydroxy-3-methylpyrimidin-4(3R)-one in 1 ml THF was added 20.3 mg (0.025 mmol) 1,1'-bis(diphenylphosphino)ferrocene-palladium(II)dichloride dichloromethane adduct, 74 mg (0.374 mmol) biphenyl-3-boronic acid, and 0.747 ml (0.747 mmol) 1 M aq Cs₂CO₃. The reaction mixture was heated to 120° C. for 20 min in the microwave, then diluted with 2 ml water, extracted with 10 ml EtOAc, dried over Na₂SO₄, filtered, and concentrated in vacuo. Purification by HPLC gave 10 mg (14% yield) of 2-biphenyl-3-yl-5-hydroxy-3-methylpyrimidin-4(3H)-one. ¹H NMR δ (ppm)(CH₃OH-d₄): 7.83-7.77 (2 H, m), 7.67 (2 H, d, J=7.69 Hz), 7.64-7.55 (2 H, m), 7.53-7.42 (3 H, m), 7.37 (1 H, t, J=7.33 Hz), 3.50 (3 H, s). HRMS (ESI positive) calc (M+H)⁺=279.1128. Found 279.1127.

Example 4

2-(3-isoquinolin-5-ylphenyl)-5-hydroxy-3-methylpyrimidin-4(3H)-one (4)

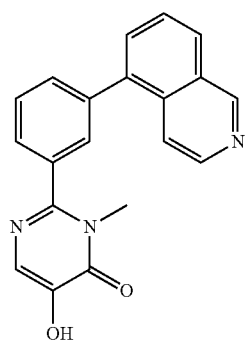

4

2-chloro-5-[(4-methoxybenzyl)oxy]-3-methylpyrimidin-4(3H)-one

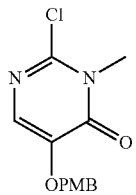

To a solution of 9.60 g (59.8 mmol) 2-chloro-5-hydroxy-3-methylpyrimidin-4(3H)-one in 300 ml DMF was added 20.4 ml (149 mmol) PMBCl, and 48.7 g (149 mmol) $Cs_2CO_3$. The reaction mixture was heated to 60° C. for 3 h, cooled to rt, quenched with 200 ml water, extracted with 500 ml EtOAc, dried over $Na_2SO_4$, filtered, and concentrated in vacuo. Purification by flash chromatography (330 g silica gel, 3-80% EtOAc:hexane) gave 10 g (60% yield) of 2-chloro-5-[(4-methoxybenzyl)oxy]-3-methylpyrimidin -4(31-1)-one. LCMS $[M+H]^+=281.0$.

2-(3-hydroxyphenyl)-5-[(4-methoxybenzyl)oxy]-3-methylpyrimidin-4(3H)-one

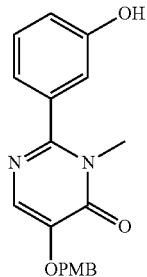

To a solution of 2 g (7.12 mmol) 2-chloro-5-[(4-methoxybenzyl)oxy]-3-methylpyrimidin-4(3H)-one in 20 ml THF was added 521 mg (0.712 mmol) 1,1'-bis(diphenylphosphino)ferrocene-palladium(II)dichloride dichloromethane adduct, 1.33 g (9.62 mmol) 3-hydroxyphenylboronic acid, and 11.4 ml (11.4 mmol) 1 M aq $Cs_2CO_3$. The reaction mixture was heated to 120° C. for 30 min in the microwave, then diluted with 10 ml water, extracted with 100 ml EtOAc, dried over $Na_2SO_4$, filtered, and concentrated in vacuo. Purification by flash chromatography (50 g silica gel, 0-100% EtOAc:hexane) gave 340 mg (14% yield) of 2-(3-hydroxyphenyl)-5-[(4-methoxybenzyl)oxy]-3-methylpyrimidin-4(3H)-one. LCMS $[M+H]^+=339.0$.

3-{5-[(4-methoxybenzyl)oxy]-1-methyl-6-oxo-1,6-dihydropyrimidin-2-yl}phenyl trifluoromethanesulfonate

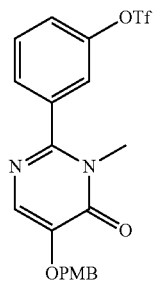

To a −78° C. solution of 320 mg (0.946 mmol) 2-(3-hydroxyphenyl)-5-[(4-methoxybenzyl)oxy]-3-methylpyrimidin-4(3H)-one in 5 ml pyridine was added 200 µl (1.18 mmol) triflic anhydride. The reaction was allowed to warm to rt over 60 min, then it was poured into 30 ml water, extracted with 100 ml $CH_2Cl_2$, dried over $Na_2SO_4$, and concentrated in vacuo. Purification by flash chromatography (12 g silica gel, 0-100% EtOAc:hexane) gave 373 mg (84%) of 3-{5-[(4-methoxybenzyl)oxy]-1-methyl-6-oxo -1,6-dihydropyrimidin-2-yl}phenyl trifluoromethanesulfonate. LCMS $[M+H]^+=470.9$.

2-(3-isoquinolin-5-ylphenyl)-5-hydroxy-3-methylpyrimidin-4(3H)-one (4)

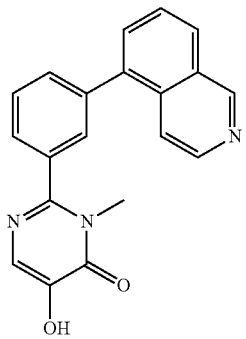

4

To a solution of 50.0 mg (0.106 mmol) 3-{5-[(4-methoxybenzyl)oxy]-1-methyl-6-oxo-1,6-dihydropyrimidin-2-yl}phenyl trifluoromethanesulfonate in 2 ml THF was added 7.8 mg (0.011 mmol) 1,1'-bis(diphenylphosphino)ferrocene-palladium(II)dichloride dichloromethane adduct, 18.3 mg (0.106 mmol) isoquinoline-5-boronic acid, and 300 µl (0.300 mmol) 1 M $Cs_2CO_3$. The reaction mixture was heated to 120° C. for 20 min in the microwave, then extracted with 10 ml EtOAc, and concentrated in vacuo. The oil was dissolved in 1 ml $CH_2Cl_2$, 1 ml TFA was added, and then concentrated in vacuo. Purification by mass-guided high throughput purification gave 15 mg (43% yield) of 2-(3-isoquinolin-5-ylphenyl)-5-hydroxy-3-methylpyrimidin-4(3H)-one. $^1H$ NMR δ (ppm) (DMSO-$d_6$): 9.62 (1 H, s), 8.58 (1 H, s), 8.34 (1 H, d, J=8.04 Hz), 7.97-7.86 (3 H, m), 7.74-7.66 (4 H, m), 7.57 (1 H, s), 2.54 (3 H, s). HRMS (ESI positive) tale $(M+H)^+=330.1237$. Found 330.1237.

Example 5

5-hydroxy-2-[3-(4-methoxyphenoxy)phenyl]-3-methylpyrimidin-4(3H)-one (5)

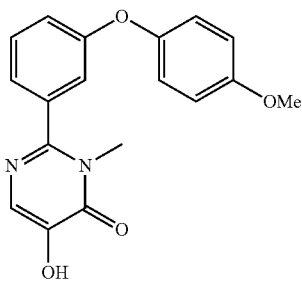

5

To a solution of 40.0 mg (0.118 mmol) 2-(3-hydroxyphenyl)-5-[(4-methoxybenzyl)oxy]-3-methylpyrimidin-4(3H)-one in 1 ml NMP was added 27.6 mg (0.118 mmol) 4-iodoanisole, 46.2 mg (0.142 mmol) Cs$_2$CO$_3$, 2.18 μl (0.012 mmol) 2,2,6,6-tetramethyl-3,5-heptanedione, and 5.85 mg (0.059 mmol) copper(I) iodide. The reaction mixture was heated to 180° C. for 30 min in microwave, diluted with 2 ml water, extracted with 10 ml EtOAc, and concentrated in vacuo. The oil was dissolved in 1 ml CH$_2$Cl$_2$, 1 ml TFA was added, and then concentrated in vacuo. Purification by mass-guided high throughput purification gave 10.0 mg (26% yield) of 5-hydroxy-2-[3-(4-methoxyphenoxy)phenyl]-3-methylpyrimidin-4(3H)-one. $^1$H NMR δ (ppm)(DMSO-d$_6$): 7.50 (1 H, s), 7.45 (1 H, t, J=7.93 Hz), 7.25 (1 H, d, J=7.66 Hz), 7.09-7.02 (4 H, m), 6.98 (2 H, d, J=8.74 Hz), 3.75 (3 H, s), 2.54 (3 H, s). HRMS (ESI positive) calc M+H=325.1181. Found 325.11.

Example 6

5-Hydroxy-2-(4-trifluoromethyl-phenyl)-3H-pyrimidin-4-one (6)

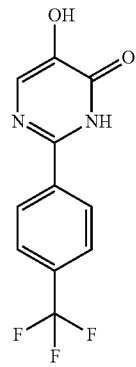

2-Chloro-4,5-dimethoxy-pyrimidine

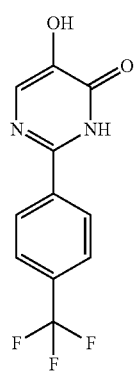

To a solution of 10 g (55.9 mmol) 2,4-dichloro-5-methoxypyrimidine in 200 mL MeOH was added 7.7 g (55.9 mmol) K$_2$CO$_3$. The reaction mixture was stirred at room temperature for 24 h, then the volatiles were removed in vacuo. The residue was diluted with EtOAc (200 mL) and water (100 mL). The organic layer was separated, dried (Na$_2$SO$_4$), and evaporated affording 9.0 g (92%) 2-chloro-4,5-dimethoxy-pyrimidine as a fluffy white solid which was used in subsequent steps without further purification. LCMS [M+H]$^+$=175.0.

5-Hydroxy-2-(4-trifluoromethyl-phenyl)-3H-pyrimidin-4-one (6)

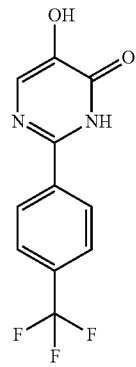

To a mixture of 0.05 g (0.26 mmol) 4-trifluoromethylphenylboronic acid, 0.02 g (0.009 mmol Pd EN Cat™ 30, and 0.65 mL 1 M aq Cs$_2$CO$_3$, was added a solution of 0.005 g (0.009 mmol) 1,1'-(bisdiphenylphosphino)ferrocene and 0.03 g (0.17 mmol) 2-chloro-4,5-dimethoxy-pyrimidine in 1 mL THF, The resulting mixture was heated by microwave to 150° C. for 10 minutes. After cooling, the aq layer was removed and the organic phase was filtered and concentrated. To the resulting residue was added 1 mL 33% HBr in AcOH, and the resulting mixture was heated by microwave to 160° C. for 5 min. The resulting solution was diluted with water (2 mL) and loaded onto an SCX column. After washing with MeOH (5 mL), the crude product was eluted off with 2 M ammonia in MeOH. Purification by automated mass-guided HPLC afforded 1.7 mg (4%) 5-hydroxy-2-(4-trifluoromethyl-phenyl)-3H-pyrimidin-4-one. NMR (499 MHz, DMSO-d$_6$): δ 9.85 (br s, 1 H); 8.22 (d, J=7.93 Hz, 2 H); 7.85 (d, J=8.12 Hz, 2 H); 7.63 (br s, 1 H). High resolution mass spec (FT/ICR) calc (M+H)$^+$=257.0533 found 257.0532.

Example 7

5-Hydroxy-2-[2-(1H-indol-4-yl)pyridin-4-yl]-3-methylpyrimidin-4(3H)-one (7)

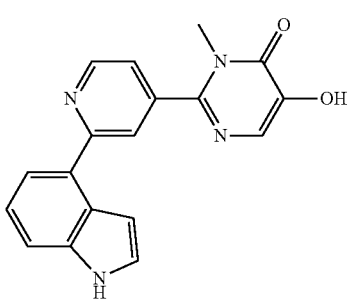

2-Chloropyridine-4-carboximidamide

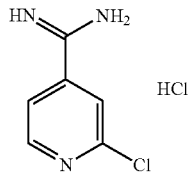

To a suspension of ammonium chloride (10.7 g, 200 mmol) in 250 mL of dry toluene. was added a 2 M solution of Al(CH$_3$) (100 mL, 200 mmol) in toluene dropwise under nitrogen at 0° C. The resulting reaction mixture was stirred at rt until no more evolution of gas was observed and then 2-chloropyridine -4-carbonitrile (13.86 g, 100 mmol) was added. The mixture was stirred at 90° C. overnight. It was then cooled down to 0° C. and 300 mL of methanol were added with subsequent stirring for 1 h at rt. After filtration, the solid was washed with methanol for several times, the solution was evaporated to dryness under vacuum. The residue was washed with methanol to give 2-chloropyridine-4-carboximidamide. (18.3 g, 95%). $^1$H NMR δ (400 MHz, d$_6$-DMSO): 8.70 (dd, J=4.8, 0.4 Hz, 1H), 8.00 (dd, J=1.6, 0.4 Hz, 1H), 7.84 (dd, J=5.2, 1.6 Hz, 1H), 7.80 (m, 1H), 7.53 (t, J=8.1 Hz, 1H); MS (ESI) m/z (M+H)$^+$ 156.

Ethyl(benzyloxy)acetate

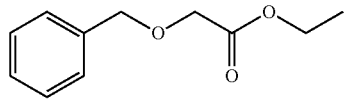

To a suspension of sodium hydride (44.2 g, 60 percent in oil, 1.1 mol) in dry toluene (800 mL) was added dropwise a solution of benzyl alcohol (108 mL, 1.0 mol, in 200 mL of toluene) at 0° C. under nitrogen over 30 min. The resulting mixture was stirred for 3.5 h at rt. The reaction was then cooled with ice water, to which a solution of ethyl bromoacetate (167.6 g, 1.0 mmol, in 200 mL of toluene) was added in 30 min and the resulting mixture was stirred for additional 25 min at 0° C. The reaction mixture was then poured into a mixed solution of 800 mL of cold water and 10 mL of cone HCl, followed by extraction with toluene. The organic layer was washed with saturated aq NaCl and dried over anhydrous MgSO$_4$. Filtration, evaporation, and purification by flash chromatography provided ethyl(benzyloxy)acetate. (98 g, 50.5%). $^1$H-NMR δ (400 MHz, CDC$_3$): 7.38-7.30 (m, 5H), 4.63 (s, 2H), 4.22 (q, J=7.2 Hz, 2H), 4.09 (s, 2H), 1.28 (t, J=7.2 Hz, 3H).

Ethyl 2-(benzyloxy)-3-oxopropanoate

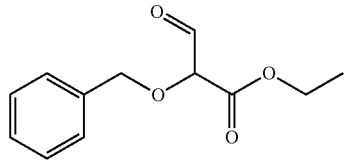 [SMILES: CCOC(=O)C(C=O)OCc1ccccc1]

To a suspension of sodium hydride (3.3 g, 60% in paraffin oil, 82.5 mmol) in dry ether (100 mL) and dry ethyl formate (5.55 g, 75 mmol) was added ethyl(benzyloxy)acetate (14.57 g, 75 mmol) dropwise with stirring. The resulting mixture solution was then refluxed for 2 h and concentrated to give crude ethyl 2-(benzyloxy)-3-oxopropanoate which was used in the subsequent step without further purification.

5-(Benzyloxy)-2-(2-chloropyridin-4-yl)pyrimidin-4-ol

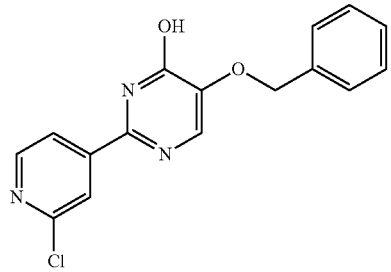 [SMILES: Oc1nc(-c2ccnc(Cl)c2)ncc1OCc1ccccc1]

A mixture of crude ethyl 2-(benzyloxy)-3-oxopropanoate (all from previous step), 2-chloropyridine-4-carboximidamide (9.57 g, 50 mmol) and 100 mL of anhydrous ethanol was refluxed for 4 h under nitrogen. The mixture was then cooled and the volatile solvents were removed by rotary-evaporator. The residue was re-dissolved in water and filtered. The filtrate was acidified by HCl (4N aq) in an ice bath and the white precipitate was filtered, washed with water, and dried to give 5-(benzyloxy)-2-(2-chloropyridin-4-yl)pyrimidin-4-ol (10.4 g, 66%). $^1$H NMR δ (400 MHz, d$_6$-DMSO): 13.12 (s, 1H), 8.58 (d, J=5.2 Hz, 1H), 8.12 (s, 1H), 8.04 (d, J=5.2 Hz, 1H), 7.94 (s, 1H), 7.51-7.34 (m, 5H), 5.20 (s, 2H); MS (ESI) m/z (M++H)$^+$ 314.

5-(Benzyloxy)-2-(2-chloropyridin-4-yl)-3-methylpyrimidin-4(3H)-one

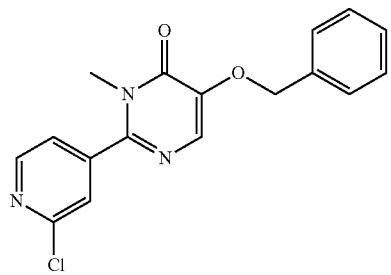 [SMILES: Cn1c(-c2ccnc(Cl)c2)ncc(OCc2ccccc2)c1=O]

To a mixture of 5-(benzyloxy)-2-(2-chloropyridin-4-yl) pyrimidin-4-ol (14.2 g, 112 mmol), Cs$_2$CO$_3$ (36.6 g, 112 mmol) in 300 mL of 1,4-dioxane, was added Me$_2$SO$_4$ (17.6 g, 56 mmol) and the resulting mixture was refluxed for 5 min. After cooling to rt, EtOAc (300 mL) and water (200 mL) were added. The organic layer was separated, the aqueous layer was extracted with EtOAc (2×100 mL). The combined organic layer was washed with water, brine, and dried over Mg$_2$SO$_4$, filtered, and concentrated to give 25 g of crude compound, which was purified by silica gel to afford 5-(benzyloxy)-2-(2-chloropyridin-4-yl)-3-methylpyrimidin-4(3H) one (4.0 g, 22%). $^1$H-NMR δ (400 MHz, d$_6$-DMSO): 8.53

(dd, J=5.2, 0.4 Hz, 1H), 7.51 (s, 1H), 7.44 (m, 3H), 7.42-7.29 (m, 4H), 5.19 (s, 2H), 3.33 (s, 3H); MS (ESI) m/z (M+H)⁺ 328.

2-(2-Bromopyridin-4-yl)-5-hydroxy-3-methylpyrimidin-4(3H)-one

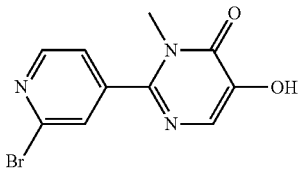 [SMILES: Cn1c(-c2ccnc(Br)c2)ncc(O)c1=O]

A mixture of 5-(benzyloxy)-2-(2-chloropyridin-4-yl)-3-methylpyrimidin-4(3H)-one (3.5 g, 10.7 mmol), conc. aq. HBr (10 mL), and HOAc (50 mL) was heated at 100° C. for 2 h with stirring. After cooled to rt, the solid was filtered, washed with EtOAc several times, dried to give 5 g of crude compound, which was purified by prep-HPLC to give pure 2-(2-bromopyridin-4-yl)-5-hydroxy-3-methylpyrimidin-4 (3H)-one (1.9 g, 623%). ¹H-NMR δ (400 MHz, d₆-DMSO): 9.88 (s, 1H), 8.52 (dd, J=5.6, 0.4 Hz, 1H), 7.86 (dd, J=5.2, 0.4 Hz, 1H), 7.65 (dd, J=5.2, 1.6 Hz, 1H), 7.54 (d, J=2.0 Hz, 1H), 3.33 (s, 3H); MS (ESI) m/z. (M+H)⁺ 282.

5-Hydroxy-2-[2-(1H-indol-4-yl)pyridin-4-yl]-3-methylpyrimidin-4(3H)-one (7)

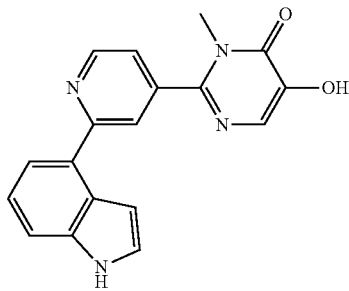

A mixture of 2-(2-bromopyridin-4-yl)-5-hydroxy-3-methylpyrimidin-4(3R)-one (30 mg, 0.106 mmol), 1H-indol-4-ylboronic acid (32 mg, 0.2 mmol), and 1,1'-bis(diphenylphosphino)ferrocene-palladium(II)dichloride dichloromethane complex (4 mg) in THF (2 mL) and 1 M aq Cs₂CO₃ (1 mL) was heated in a. microwave at 160° C. for 10 min. After cooling to rt, the THF layer was separated and the aq. solution was extracted with THF (2 mL). The combined THF solution was treated with QuadraPure TU resin (Aldrich), filtered, and concentrated. The concentrated residue was purified by LCMS to give 5-hydroxy-2-[2-(1H-indol-4-yl)pyridin-4-yl]-3-methylpyrimidin-4(3H)-one (26.5 mg, TFA salt). ¹H-NMR (499 MHz, d₆-DMSO): δ 11.31 (s, 1 H); 9.77 (s, 1 H); 8.85 (d, J=5.0 Hz, 1 H); 8.08 (s, 1 H); 7.61-7.56 (m, 2 H); 7.56-7.50 (m, 2 H); 7.46 (t, J=2.7 Hz, 1 H); 7.22 (t, J=7.7 Hz, 1 H); 6.99-6.96 (m, 1 H); 3.44 (s, 3 H); HRMS calculated for (C18H14N4O2+H)⁺ 319.1190, found 319.1188.

Assays

The activity of the compounds in accordance with the present invention as COMT inhibitors may be readily determined without undue experimentation using a fluorescence or fluorescence polarization (FP) methodology that is well known in the art (Kurkela M et al., Anal Biochem (331) 2004, 198-200 and Graves, T L et al., Anal Biochem (373) 2008, 296-306). Assays utilized purified human COMT enzyme of the Val158 variant (membrane-bound MB-COMT or soluble S-COMT) containing a C-terminal 6 or 10-histidine tag. Compounds of the following examples had activity in reference assays by exhibiting the ability to inhibit the methylation of esculetin and/or inhibit the production of S-adenosyl-homocysteine (SAH). Any compound exhibiting an IC₅₀ below 1 μM would be considered a COMT inhibitor as defined herein.

In a typical experiment the COMT inhibitory activity of the compounds of the present invention was determined in accordance with the following experimental methods detailed below. The fluorescence assay was based on methylation of a substrate (6,7-dihydroxycoumarin or 'esculetin') by COMT to produce a highly fluorescent product (7-hydroxy-6-methoxycoumarin or 'scopoletin'). The reaction requires the presence of magnesium ions and a methyl donor, in this case S-adenosylmethionine (SAM). A 10 mM compound stock in DMSO was used to prepare 10 point 3-fold dilution series and 1 uL of appropriate dilution was plated into assay wells (black 96 well round bottom polystyrene plates from. Costar; catalog #3792). Recombinant enzyme was diluted in assay buffer (100 mM Na₂HPO₄ pH 7.4, 1 mM DTT, 0.005% Tween-20) and 35 μL was added to assay wells containing 1 μL of compound. Preincubation of COMT enzyme and compound proceeded for 2 hours at room temperature. Enzyme assays were initiated with 5 uL of a mixture containing 40 μM SAM (USB catalog # US10601), 4 μM esculetin (substrate) and 40 mM MgCl₂. The formation of product (seopoletin) was monitored over time by fluorescence (excitation 340 nm, emission 460 nm, no lag, 100 μs integration time, 5 flashes, top read) using a Tecan Safire² plate reader. Assays were monitored over time until a signal to background of 4 to 1 was achieved. Titration curves and IC₅₀ values were calculated using standard procedures. Briefly, data were calculated as (mean of test wells)–(mean of no-enzyme controls)/(mean of total enzyme controls)–(mean of no-enzyme controls), then expressed as a percentage and subtracted from 100 to give percent inhibition of COMT activity. In some cases, compounds were not pre-incubated with MB-COMT for 2 hours at room temperature prior to starting the enzyme assays.

To determine IC₅₀ values in the fluorescence polarization assay, solutions of test compounds were prepared and preincubated with COMT enzyme as stated above. Enzyme reactions were initiated upon the addition of 5 μL of an 8× mix prepared in assay buffer containing 8 μM SAM (USB catalog # US10601), 16 μM dopamine (Sigma catalog # H8502) and 40 mM MgCl₂. After 25 minutes incubation at room temperature, reactions were quenched with 5 μL 250 mM EDTA, pH 82. To quenched reactions, 20 μL of a preformed complex containing S-adenosyl-L-cysteine (SAC) TAMRA tracer (2 mM from Ana spec diluted 1:80,000) and a 1:20 dilution of anti-S-adenosyl-L-homocysteine antibody (mouse monoclonal from Abbott Homocysteine detection kit, catalog #7D29-20) was prepared in assay buffer 11 (Na₂HPO₄ pH 7.2). Prior to combining with quenched enzyme assays, the SAH antibody/SAC TAMRA tracer complex was preformed at room temperature for 30 minutes while protected from light. Therefore, the final concentration of the SAH antibody/SAC TAMRA mix was 1:60 and 1:240,000, respectively. After a 2.5 hour incubation at room temperature, protected from light, fluorescence polarization was measured using a Tecan Safire[2] plate reader (excitation 530 nm, emission 595 urn). Titration curves and $IC_{50}$ values were calculated using standard protocols.

The compounds of formula I have an $IC_{50}$ activity of 100 μM or less for COMT. Many of the compounds of formula I have an 1050 of less than 200 nM. For example, the compounds below have $IC_{50}$<600 nM in the "Esculetin or Fluorescence Polarization assay". In particular, the compounds of the Examples beginning on page 38 of the specification, Examples 1, 3, 5, 6, and 8 exhibited the following $IC_{50}$ (nM) values:

| Example# | MB-COMT IC50-(nM) |
|---|---|
| 1 | 180 |
| 3 | 170 |
| 5 | 93 |
| 6 | 210 |
| 8 | 590 |

What is claimed is:

1. A compound of structural formula I:

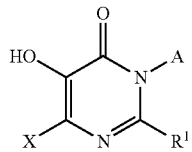

I including tautomers or a pharmaceutically acceptable salt, an individual enantiomer or a diastereomer thereof wherein:

A represents hydrogen, or $C_{1-6}$ alkyl, said alkyl optionally substituted with 1 to 3 groups independently selected from halo, OH, or Oalkyl;

X represents hydrogen, OH, halo, $OC_{1-6}$ alkyl, $NR^2R^3$, or $(CH_2)_nC_{6-10}$ aryl, said alkyl and said aryl optionally substituted with 1 to 3 groups of $R^a$;

$R^1$ represents $C_{6-10}$ aryl or $(CH_2)_n$heterocyclyl, said aryl and heterocyclyl substituted with 1 to 3 groups of $R^a$;

$R^2$ and $R^3$ independently represent H, OH, $C_{1-6}$ alkyl, $N(CH_3)_2$, $(CH_2)_n$ heterocyclyl, or $(CH_2)_nC_{6-10}$ aryl, said aryl and heterocyclyl optionally substituted with 1 to 3 groups of $R^a$; or $R^2$ and R3 together with the nitrogen atom to which they are attached form a 5-10 membered ring that is optionally substituted with 1 to 3 groups independently selected from halo, OH, C2-6 alkenyl, $(CH_2)_n$heterocyclyl or $(CH_2)_nC_{6-10}$ aryl;

each $R^a$ independently represents $C_{1-6}$ alkyl, halogen, $C_{2-4}$alkynyl, $(CH_2)_nCF_3$, $OCHF_2$, $OCF_3$, $C_{3-6}$ cycloalkyl, $O(CH_2)_nC_{3-6}$ cycloalkyl, $NR^2C(O)R^2$, $C(O)N(R^2)_2$, $C(R^2)_2OR^2$, $C(O)R^2$, $NO_2$, CN, $N(R^2)_2$, $(CH_2)_nC(O)OR^2$, $SO_2R^2$, $NHSO_2R^2$, $OC_{1-6}$ alkyl, $(CH_2)_n$ heterocyclyl, $NH(CH_2)_n$heterocyclyl, $(CH_2)_nC_{6-10}$ aryl, $O(CH_2)_nC_{6-10}$ aryl, or $O(CH_2)_n$ heterocyclyl, said alkyl, alkynyl, cycloalkyl, heterocyclyl and aryl optionally substituted with 1 to 3 groups of $R^b$;

each $R^b$ independently represents $C_{1-6}$ alkyl, $OC_{1-6}$ alkyl, halogen, $CHF_2$, $OCHF_2$, —O—, $N(R^2)_2$, $CH_2OH$, $S(O)_2NR^2R^3$, $(CH_2)_nC_{6-10}$ aryl, $(CH_2)_n$ heterocyclyl, $C(O)(CH_2)_n$ heterocyclyl, $NH(CH_2)_n$heterocyclyl, $C(O)$ $NHC_{3-6}$cycloalkyl, $OR^2$, $C_{3-6}$cycloalkyl, $(CH_2)_nCF_3$, or CN, said heterocyclyl optionally substituted with 1 or more of $C_{1-6}$ alkyl; and n represents 0 to 5.

2. The compound according to claim 1 wherein $R^1$ is phenyl or pyridyl, both substituted with 1 to 3 groups of $R^a$.

3. The compound according to claim 1 wherein the $R^a$ substituent on $R^1$ is selected from the group consisting of $C_{1-6}$alkyl, $NHSO_2R^2$, halo, CN, $(CH_2)_nC_{6-10}$aryl, heterocyclyl, $C_{2-4}$alkynyl, $OC_{1-6}$alkyl, and $OC_{6-10}$aryl, said alkyl, alkynyl, aryl and heterocyclyl optionally substituted with 1 to 3 groups of $R^b$.

4. The compound according to claim 3 wherein the $R^b$ substituent on the $R^a$ of $R^1$ is selected from the group consisting of H, halo, $(CH_2)_nC_{6-10}$aryl, $(CH_2)_n$heterocyclyl, $C_{1-6}$alkyl, $OC_{1-6}$alkyl, $OCHF_2$, and $CF_3$.

5. The compound according to claim 1 represented by structural formula Ia:

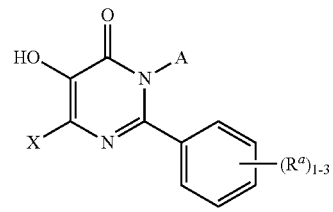

Ia including tautomers or a pharmaceutically acceptable salt, an individual enantiomer or a diastereomer thereof wherein A is $C_{1-6}$ alkyl optionally substituted with 1 to 3 groups independently selected from halo, OH, or Oalkyl, X is hydrogen, and each $R^a$ is independently selected from the group consisting of $C_{1-6}$alkyl, $NHSO_2R^2$, halo, CN, $(CH_2)_nC_{6-10}$ aryl, heterocyclyl, $C_{2-4}$alkynyl, $OC_{1-6}$alkyl, and $OC_{6-10}$aryl, said alkyl, alkynyl, aryl and heterocyclyl optionally substituted with 1 to 3 groups of $R^b$, and each $R^b$ is independently selected from the group consisting of halo, $(CH_2)_nC_{6-10}$ aryl, $(CH_2)_n$heterocyclyl, $C_{1-6}$alkyl, $OC_{1-6}$alkyl, $OCHF_2$, and $CF_3$.

6. The compound according to claim 1 represented by structural formula Ib:

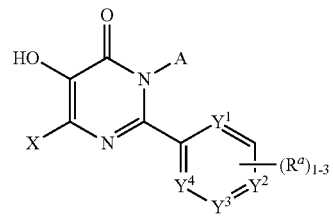

Ib including tautomers or a pharmaceutically acceptable salt, an individual enantiomer or a diastereomer thereof wherein one of $Y^1, Y^2, Y^3$ and $Y^4$ is N while the others are CH, A is $C_{1-6}$ alkyl optionally substituted with 1 to 3 groups independently selected from halo, OH, or Oalkyl, X is hydrogen, and $R^a$ is selected from the group consisting of $C_{1-6}$ alkyl, $NHSO_2R^2$, halo, CN, $(CH_2)_n$ $C_{6-10}$ aryl, heterocyclyl, $C_{2-4}$alkynyl, $OC_{1-6}$alkyl, and $OC_{6-10}$aryl, said alkyl, alkynyl, aryl and heterocyclyl optionally substituted with 1 to 3 groups of $R^b$, and $R^b$ is selected from the group consisting of halo, $(CH_2)_nC_{6-10}$ aryl, $(CH_2)_n$heterocyclyy, $C_{1-6}$alkyl, $OC_{1-6}$alkyl, $OCHF_2$, and $CF_3$.

7. The compound according to claim 6 wherein $Y^2$ is N and $Y^1$, $Y^3$ and $Y^4$ are all CH.

8. The compound according to claim 1 represented by structural formula IIa

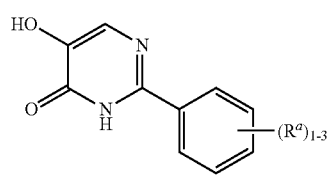

IIa including tautomers or a pharmaceutically acceptable salt, an individual enantiomer or a diastereomer thereof wherein $R^a$ is selected from the group consisting of $C_{1-6}$alkyl, $NHSO_2R^2$, halo, CN, $(CH_2)_nC_{6-10}$ aryl, heterocyclyl, $C_{2-4}$alkynyl, $OC_{1-6}$alkyl, and $OC_{6-10}$aryl, said alkyl, alkynyl, aryl and heterocyclyl optionally substituted with 1 to 3 groups of $R^b$, and $R^b$ is selected from the group consisting of halo, $(CH_2)_nC_{6-10}$ aryl, $(CH_2)_n$ heterocyclyl, $C_{1-6}$alkyl, $OC_{1-6}$alkyl, $OCHF_2$, and $CF_3$.

9. The compound according to claim 1 represented by structural formula IIb:

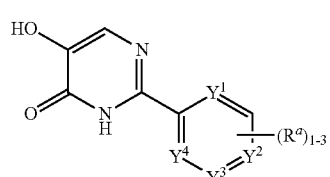

IIb including tautomers or a pharmaceutically acceptable salt, an individual enantiomer or a diastereomer thereof wherein one of $Y^1$, $Y^2$, $Y^3$ and $Y^4$ is N while the others are CH, $R^a$ is selected from the group consisting of $C_{1-6}$ alkyl, $NHSO_2R^2$, halo, CN, $(CH_2)_nC_{6-10}$ aryl, heterocyclyl, $C_{2-4}$alkynyl, $OC_{1-6}$alkyl, and $OC_{6-10}$aryl, said alkyl, alkynyl, aryl and heterocyclyl optionally substituted with 1 to 3 groups of $R^b$, and $R^b$ is selected from the group consisting of halo, $(CH_2)_nC_{6-10}$ aryl, $(CH_2)_n$heterocyclyl, $C_{1-6}$alkyl, $OC_{1-6}$alkyl, $OCHF_2$, and $CF_3$.

10. The compound according to claim 9 wherein $Y^2$ is N and $Y^1$, $Y^3$ and $Y^4$ are all CH.

11. A pharmaceutical composition comprising an inert carrier and an effective amount of a compound according to claim 1.

12. A method of treating a disease or disorder selected from the group consisting of schizophrenia, bipolar disorder, major depressive disorder, ADD, ADHD, dementia, Parkinson's disease, Huntington's disease, obsessive-compulsive disorder, and anxiety disorder, in a human comprising administering to said human a therapeutically effective amount of a compound according to formula I in claim 1 or a pharmaceutically acceptable salt, an individual enantiomer or a diastereomer thereof.

13. The composition according to claim 11 further comprising one or more therapeutically active compounds selected from the group consisting of opiate agonists or antagonists, calcium channel antagonists, 5HT, $5\text{-}HT_{1A}$ complete or partial receptor agonists or antagonists, sodium channel antagonists, N-methyl-D-aspartate (NMDA) receptor agonists or antagonists, COX-2 selective inhibitors, neurokinin receptor 1 (NK1) antagonists, non-steroidal anti-inflammatory drugs (NSAID), selective serotonin reuptake inhibitors (SSRI) and/or selective serotonin and norepinephrine reuptake inhibitors (SSNRI), tricyclic antidepressant drugs, norepinephrine modulators, lithium, valproate, norepinephrine reuptake inhibitors, monoamine oxidase inhibitors (MAOIs), reversible inhibitors of monoamine oxidase (RIMAs), alpha-adrenoreceptor antagonists, atypical anti-depressants, benzodiazepines, corticotropin releasing factor (CRF) antagonists, neurontin (gabapentin) and pregabalin.

14. The compound according to claim 1 including tautomers or a pharmaceutically acceptable salt, an individual enantiomer or a diastereomer thereof wherein:

X represents hydrogen, OH, halo, $OC_{1-6}$ alkyl, or $NR^2R^3$, said alkyl optionally substituted with 1 to 3 groups of halogen, $(CH_2)_nCF_3$, $OCHF_2$, $OCF_3$, $C_{3-6}$ cycloalkyl, $O(CH_2)_nC_{3-6}$ cycloalkyl, CN, $N(R^2)_2$, $(CH_2)_nC(O)OR^2$, $OR^2$, $(CH_2)_n$ heterocyclyl, $(CH_2)_nC_{6-10}$ aryl, $O(CH_2)_n$ $C_{6-10}$ aryl, or $O(CH_2)_n$ heterocyclyl, said heterocyclyl and aryl optionally substituted with 1 to 3 groups of $C_{1-6}$ alkyl, $OC_{1-6}$ alkyl, halogen, $CHF_2$, $OCHF_2$, —O—, $OR^2$, $C_{3-6}$cycloalkyl, $(CH_2)_nCF_3$, or CN; and $R^1$ represents phenyl or pyridyl, said phenyl and pyridyl substituted with 1 to 3 groups of $R^a$.

15. The compound according to claim 14 including tautomers or a pharmaceutically acceptable salt, an individual enantiomer or a diastereomer thereof wherein:

A represents hydrogen;

X represents hydrogen;

$R^1$ represents phenyl substituted with 1 to 3 groups of $C_{1-6}$ alkyl, halogen, $CF_3$, $OCHF_2$, $OCF_3$, $OR^2$ or CN, said alkyl optionally substituted with 1 to 3 groups of halogen; and $R^2$ represents $C_{1-6}$ alkyl.

16. The compound according to claim 14 including tautomers or a pharmaceutically acceptable salt, an individual enantiomer or a diastereomer thereof wherein:

A represents $C_{1-6}$ alkyl;

X represents hydrogen;

$R^1$ represents phenyl substituted with 1 to 3 groups of $C_{1-6}$ alkyl, halogen, $CF_3$, $OCHF_2$, $OCF_3$, $OR^2$ or CN, said alkyl optionally substituted with 1 to 3 groups of halogen; and $R^2$ represents $C_{1-6}$ alkyl.

17. The method of claim 12, wherein the disease or disorder is selected from the group consisting of schizophrenia, major depressive disorder, ADD, ADHD, and Parkinson's disease.

18. The method of claim 12, further comprising administering to said human a therapeutically effective amount of an anti-depressant, wherein said anti-depressant is administered separately or in conjunction with the compound according to formula I in claim 1 or a pharmaceutically acceptable salt, an individual enantiomer or a diastereomer thereof.

* * * * *